(12) United States Patent
DiSpirito et al.

(10) Patent No.: US 8,735,538 B1
(45) Date of Patent: May 27, 2014

(54) USE OF METHANOBACTIN

(75) Inventors: Alan Angelo DiSpirito, Ames, IA (US);
Dong-Won Choi, Ames, IA (US);
Jeremy David Semrau, Ann Arbor, MI (US); David Keeney, Ann Arbor, MI (US)

(73) Assignees: Iowa State University Research Foundation, Inc., Ames, IA (US); The Regents of the University of Michigan, Ann Arbor, MI (US)

( * ) Notice: Subject to any disclaimer, the term of this patent is extended or adjusted under 35 U.S.C. 154(b) by 24 days.

(21) Appl. No.: 12/970,180

(22) Filed: Dec. 16, 2010

Related U.S. Application Data

(62) Division of application No. 11/880,886, filed on Jul. 24, 2007, now Pat. No. 7,932,052.

(60) Provisional application No. 60/833,067, filed on Jul. 24, 2006.

(51) Int. Cl.
*A61K 31/28* (2006.01)
*C07K 7/00* (2006.01)
*A01N 55/02* (2006.01)

(52) U.S. Cl.
USPC ........... 530/206; 530/327; 514/16.6; 514/495

(58) Field of Classification Search
CPC ............ A61K 31/28; C07K 7/00; C12Q 1/10; C12P 3/00; C22C 5/02
See application file for complete search history.

(56) References Cited

U.S. PATENT DOCUMENTS

| | | | | |
|---|---|---|---|---|
| 5,716,612 | A | * | 2/1998 | Rybak et al. ................. 424/85.2 |
| 6,114,367 | A | * | 9/2000 | Cohan et al. ................. 514/378 |
| 7,199,099 | B2 | | 4/2007 | DiSpirito et al. |
| 7,922,788 | B2 | * | 4/2011 | Hillier et al. .................... 75/711 |
| 7,932,052 | B1 | | 4/2011 | DiSpirito et al. |

OTHER PUBLICATIONS

Hakemian et. al. The Copper Chelator Methanobactin from Methylosinus trichosporium OB3b Binds Copper(I), J Am Chem Soc.; 127(49): 17142-17143, Dec. 14, 2005.*
www.siliconfareast.com/ox_potential.htm. , last visited Jul. 9, 2012.*
Hakemian et. al. The Copper Chelator Methanobactin from *Methylosinus trichosporium* OB3b Binds Copper(I), J Am Chem Soc.; 127(49): 17142-17143, Dec. 14, 2005.*
Paciotti et. al. Colloidal Gold: A Novel Nanoparticle Vector for Tumor Directed Drug Delivery, Drug Delivery, 11:169-183, 2004.*
www.siliconfareast.com/ox_potential.htm, last visited Jul. 9, 2012.*
Paciotti et. al. Colloidal Gold: A Novel Nanoparticle Vector for Tumor Directed Drug Delivery, Drug Delivery, 11:169-183, 2004).*
Hakemian et. al. The Copper Chelator Methanobactin from *Methylosinus trichosporium* OB3b Binds Copper(I), J Am Chem Soc.; 127(49): 17142-17143, (Dec. 14, 2005).*
Silicon Far East_Oxidation Potential www.siliconfareast.com/ox_potential.htm.*
Russier-Antoine (Wavelength dependence of the hyper Rayleigh scattering response from gold nanoparticles, Journal of Chemical Physics, vol. 120, No. 22, Jun. 8, 2004).*
Hakemian et. al., The Copper Chelator Methanobactin from *Methylosinus trichosporium* OB3b Binds Copper(I). Am. Chem. Soc. Dec. 14, 2005; 127(49): 17142-17143.*
Hakemian, A. S, et al., "The Copper Chelator Methanobactin from *Methylosinus trichosporium* OB3b Binds Copper(I)", Journal of the American Chemical Society, 127(49), (2005), 17142-17143.
Paciotti, G. F, et al., "Colloidal gold: a novel nanoparticle vector for tumor directed drug delivery", Drug Deliv., 11(3), (May-Jun. 2004), 169-83.
"U.S. Appl. No. 11/880,886, Notice of Allowance", 9 pgs, Sep. 21, 2010.
"U.S. Appl. No. 11/880,886, Response to Restriction Requirement, filed May 24, 2010", 6 pgs.
"U.S. Appl. No. 11/880,886, Restriction Requirement mailed Apr. 19, 2010", 7 pgs.
Choi, D. W., et al., "Spectral and Thermodynamic Properties of Ag(I), Au(III), Cd(II), Co(II), Fe(III), Hg(II), Mn(II), Ni(II), Pg(II), U(IV), and Zn(II) Binding by Methanobactin From *Methylosinus trichosporium* OB3b", Journal of Inorganic Biochemistry, 100, (2006), 2150-2161.
Choi, D. W., et al., "Spectral, Kinetic, and Thermodynamic Properties of Cu(I) and Cu(II) Binding by Methanobactin from *Methylosinus trichosporium* OB3b", Biochemistry, 45, (2006), 1442-1453.

* cited by examiner

*Primary Examiner* — James H Alstrum Acevedo
*Assistant Examiner* — Jeanette Lieb
(74) *Attorney, Agent, or Firm* — Schwegman Lundberg & Woessner, P.A.

(57) ABSTRACT

The invention provides compositions comprising and methods employing methanobactin, as well as methanobactin synthetase sequences.

17 Claims, 20 Drawing Sheets mesA (SEQ ID NO:1):

```
   1  AGCCCGGCTG GTTCTCGTAG GCTCTCGAAA CGGCGCCCGG GNACGCCGGT
  51  TCTGACCATC GATGTGCTGA GCGAAGCGGA GCGCCATCGG CTTCTCGTCG
 101  ACTGGAACGA CACAGCCGCC GCCTATCCGC AGGACCGCTG CATTCATCAG
 151  CTGTTCGAGG CGCAGGCGAG CGAGACGCCC GACGCTGTCG CGGTGGCGTT
 201  CGAGGAGCAA AGCCTGACCT ATGCCCAATT GAACGCCAGA GCCAATCGGC
 251  TGGCGCATCA TCTGCGTCGT CTCGGAGTAG CCCCGAGAC GCTGGTCGGC
 301  CTCTGCGTCG AGCGCTCGCT CGAGATGATC GTCGGGCTGC TCGGCATAAT
 351  GAAGGCCGGC GGCGCCTATC TGCCGCTCGA CCCCGATTAT CCGGCAGATC
 401  GGCTTGCTTT CATGCTCGCC GACGCGCGGC CGCTCTTGAT CCTGACGCAA
 451  GAGCGTCTGC GCCAGCGCCT GCCGAAGGAC GCCGCGACGC TGAGCCTGGA
 501  TGTAGAGGCC GACTGGCCGT CCATCGCCGA AAGCCGCGAG GACAATCCCG
 551  AGAATCTCGC GCACCCCCAA AACCTCGCCT ATGTCATCTA CACCTCCGGA
 601  TCGACAGGCA AGCCAAAAGG CGTCGGGGTC GCGCATGACG GTCTCGTCAA
 651  TCGCATCGAC TGGATGCAGA AGCATTATCG CCTGACCGAT GACGACGTCG
 701  TGCTACAGAA GACGCCATTC AGCTTCGACG TATCGGTATG GGAGTTTTTC
 751  TGGCCTCTTC TGACCGGCGC CCGTCTCGTC CTCGCCGCGC CGGGCGATCA
 801  TCGTGAGCAG GGCCGCTTGG CGAAGCTCAT CGAAAGCCGC GCGGTCACGA
 851  CCCTGCATTT CGTGCCGACC ATGTTGACGG CGTTCTTGAA CGCTGTCGAA
 901  GGGAAGCGGA TGCGCTCGCT TCGCCGAGTG ATCTGCAGCG GCGAAGAGCT
 951  TTCCGATAGC GCCGTCTCGA AGTTCCATGA GATGGCGTAT CGTGAAAATA
1001  TGGCGTCCTG TGAGCTTCAC AACCTCTATG CCCAACCGA AGCCTCTATC
1051  GACGTCACGG CCTATTGCTG CGTCGATGAC GGCGGCATCG ACAGGGTTCC
1101  GATCGGCCGC CCGATCGCGA ACACGAAAAT CTATCTTCTC GACAAGGCTC
1151  TCCAGCCGGT TCCGATAGGG GTTTCGGGCG AGCTCTACAT TGGCGGGGTC
1201  GGCCTGGCGC GAGGCTATCT GAACCGCCCC GACCTCACGG CGGAAAGATT
1251  TGTTCCAAGC CCGTTCGGGG CTCCCGGGGA ACGTCTCTAT CGGACGGGCG
```

*FIG. 16*

```
1301  ATCTCGCGCG CTATCGTCGG GATGGGAACA TCCAATATCT CGGCCGCGCC

1351  GATCATCAGG TGAAGATCCG CGGGTTTCGC ATCGAGCTCG GCGAGATCGA

1401  GGCGGCGCTG GGGCGTCTGG AGACAGTGCG CGAAGCGGCA GCGCTGGCGC

1451  GGGAGGACGA GTCGGGCGAT AAGCGCATCG TCGCTTATGT CGTCTGCGAG

1501  GATGGGGCGG AAGCGAATGT CGCGCAGCTG CGCGCCTCGC TGGCGAAGGA

1551  TCTGCCCGAC TATATGATCC CCTCGGCTTT CGTTTTCCTC GACAGCTTGC

1601  CGCTGACGCA AAATGGCAAG ATCGACCGCA AGG
``` mesB (SEQ ID NO:2):

```
   1  ATCGTTCGTC AACGCGCATT CGCGCAAGCT CGACAGCCAT TCGATCTCGC
  51  GAACGGCCCT GTCATTCGCG TTCAGCTGCT GATACTCCCG TCTGTGGACG
 101  CGACCGCGGA TCATGTCCTG ATCATTGTTT TCCATCATAT CGTGACCGAC
 151  GACTGGTCGT CGGCCCTATT CTTAACGAG CTCGCGACCA TTTATCCTGC
 201  GTTCGCGAGC GGAAGACCGT CTCCCTGCC AGAACCCGAG CTCCAATATG
 251  TCGATTTTGC CGTTGCTCAA CGCAAATGGC TCGACGGAGA TACGCTCGAG
 301  AGACATTTAG CCTATTGGCG TGAAAAGCTC GCTGGCGGCT CTCCCTCGAT
 351  CGATCTCCCA ACGCGACGCG ATGGCGACGC CGGATTGCAG AAGACCGGTG
 401  GCGAGGTCCA TTTCGAGATC GCTGAAAAGG TCAAACGCCA ATTAACTCGG
 451  TTGAGCGAGC AGAGTAGTTA TACGCGTTTT GTCATATTCA TGTCTGCGTT
 501  CTACGTATTT CTGTTCCGCT ACACACACCA GACCGACATC TGCGTCGGGG
 551  CGCCGATCGC CAACCGCAAC CTGCGAGAAG TGGAAGATAT CCAGGGATTC
 601  TTCGTCAACA CGCTCGTATT GCGCGCAAAA TTGAGCGGCG ATCAGCGATT
 651  CTCCGCATTG CTCGAGCAGG TGCAAACCCT TGCTCTGGAG GCGCAGACAC
 701  ATCAAGATCT ACCCTTCGAG CGGCTCGTCG AGGCGCTGGG CCCACAAATT
 751  CGCACATTCG GGATCAATCC GCTTTTCCGA GTGGCGTTCG TATTTCACAA
 801  TATCGGTTTT GAAGACCCCA AAATACCGGG ATTCGATGTT GAAATAGTAC
 851  AGGGCGTCAG ACGAAACGCC GTCTTCGATC TCGTCTTGCA CATTGCCGAA
 901  AACGAAAAGG GGCTGAGAGG CTGGTTCGAA TACGATATGG GTTTGTTCGA
 951  GGACGCAACT GTCGAACGGA TGGCGCGGCA CTTTCAGAAT CTTCTGGAGA
1001  GCGCCTCGAG CAAAAGCGAC TCGCGGATAT CAGAGCTCTC TCTTTTGGAC
1051  GAGACGGAGC GCCATCGGCT TCTTGTCGAC TGGAACGACA CAGCCGCCGC
1101  CTATCCGCAG GACCGCTGCA TTCATCAGCT GTTCGAGGCG CAGGCGAGCG
1151  AGACGCCCGA CGCTGTCGCG GTGGCGTTCG AGGAGCAAAG CCTGACCTAT
1201  GCCCAATTGA ACGCCAGAGC CAATCGGCTG GCGCATCATC TGCGTCGTCT
1251  CGGAGTGGGC CCCGAGACGC TGGTCGGCCT CTGCGTCGAG CGCTCGCTCG
1301  AGATGATCGT CGGGCCGCTC GGCATAATGA AGGCCGGCGG CGCCTATCTG
1351  CCGCTCGATC CCGATTATCC GCTCGAGCGC CTCGCCTATA TGCTCGCCGA
1401  CGCGCGGCCG CTGGCGATCC TCACGCAAGA GCGGCTGCGC CAGCGTCTGC
1451  CGGACGATGT CGAGACGCTG AGCCTCGACG CCGACTGGCC GTCCATCGCC
1501  GAAAGCCGCG CGGACAATCC CGACAATCTC GCGCATCCCC AAAACCTCGC
1551  CTATGTCATC TACACCTCGG GAAGGACAGG CAAGCCGAAG GGCGTCGGGG
1601  TCACGCACCA AAATGTTCGC CGGCTCTTTG CAGCCGCCGA AGAGGCGTTT
1651  GATTTTTCCT GCGATGATGT CTGGACGCTG TTCCACTCGT TTGCGTTCGA
1701  CTTTTCTGTC TGGGAGATAT GGGGCGCGCT CCTCTATGGC GGAAGGCTGA
1751  TCATCCCGTC TTACTGGGTG ACACGATCGC CGGAAGCATT TTATGACCTA
1801  TTGTGCTCAC AGTCCGTCAC GGTTCTGAAT CAGACGCCTT CGAGCTTCTA
1851  TCAACTATCG ATTGTCGATG CGGCCCGCAA AGGAAGCGAA TTAGAGCGCT
1901  TTCCGATCGA ACGGAATCGT TCGATCGATC AGAATTCGCT CAAACGAAAG
1951  AATTCTAGAG GGCTATCCGA TCCAATCGGA TCGGATAGCC CTCTATCCTC
2001  GTTGAGGCTC GTTATTTTCG GTGGGGAAGC TCTGGAAACC GGGCGGCTGA
```

```
2051  AGGAGTGGTT CAGCCGACAT GGCGATAAAC AGCCTCAACT CGTCAACATG
2101  TATGGCATCA CGGAAACCAC GGTGCATGTC ACATTAGGGC CGCTGCAGCG
2151  CGACAGCGCA GGCGGAGTCG GGCGTCCTCT CGACGATCTC CAAGCGCTCA
2201  TACTCGACCG GAGCTCGAGT CTTCTGCCCA TCGGGGTTTC CGGAGAGCTC
2251  TACATCGGCG GGGCGGGGCT CGCGCGAGGT TATCTGGGCC GAGCGGATCT
2301  CACGGCGGAA AGATTCGTCC CCCAATCCGT TCGGAGAGCC TGGGGAGCGT
2351  CTTTTACCGC ACCGGCGATC TGGCGCGTTA TAGGGCGGAC GGAAACATCG
2401  AGTATCTCGG CCGCGCCGAT CATCAGGTGA
```

*mesC* (SEQ ID NO:3):

```
   1  ATCGCCGTCG TCGCCGAGGA TGGATCGCTG ACCTATGGCG AATTGCGTCT

51  GCGCGCCAAT CAAATCGCGC GCCTGCTGCA ACGAGCGGGA ATAGGGCCGG

101  AGACGCCCGT CGGCGTGCTC CTCGATCCCG GACTGGATTA TGTCGCGTCT

151  GTGCTCGGCG TGCTCGTGGC GGGCGGCGCC TTCGTTCCGC TGGACCCGGC

201  CTATCCGTCG GAGCGGCTGC GTTACATGCT CGCAGATTCC GGCGCGCGCG

251  CCTTGATCTC CGCGCAAAGC CTGCCACGCC TCGACTGCGT GATTCCTAAG

301  ATTCTCGTCG ACGCCGACGA GCTCGCGGAT GTTTCGAATG ACGCCGTGGT

351  CTCCAGTGCC CATCCCGACA ACCTCGCTTA TCGTCTAC ACCTCCGGCT

401  CCACGGGAGG CGCCAAAGGC GTGATGGCGA CGCATCGCAA TGCGGTCGCG

451  TCCCTCCTCG CGCGCTTCGC CTTCTATCCG CAGACGGTCG ACGACTTTCT

501  GCTTCTCTCC TCGCTTTCCT TCGACAGCTC CTTTGCGGGA TTATTCTGGA

551  CGCTGGCGCG CGGCGGACGG CTCCATCTCG TCGCCGAGAC GACGCGCCGC

601  GATCCGTCG CGTTGAAGGA GATCATCGCG AGCCGCGACA TCACCCATTT

651  CCTCTGTCTC CCCTCCTTCC ACCGCGAGCT GCTCGGAGAG CTCTCGCGCG

701  GAGAGCGGAC GATGCTGAAA TGCTGCATCG TCGCCGGCGA GGCCTGCGGC

751  GCCGATGTGG TCGAGCGCCA TTTTCACACG CTTCCAGAAG CAGCGCTGAT

801  CAATGAATAT GGTCCGACGG AATGCTCGGT CTGGTGCGCC GCCGAGCAGC

851  TGAGCACGGA AGACGATCTC TCATCGGGCG TCAGCATCGG CCGCGCGATT

901  CCCGGCTCTC GCGCTTATGT TCTCGATGAA AATGGCGAAC TCGCGCCAGT

951  CGGAATCGCC GGCGAGCTCT GCGTGGGCGG AGCAGGAGTC GCGCGCGGCT

1001  ATCGCGGCGG CGCGGAGCTG ACCGCGACGA AATTCACACC CGATCCGTTC

1051  GGCTTCGGCG AGCGTCTCTA TCGCACCGGG GATCGCGCGA GATATCGCGC

1101  GGaTGGAAAG CTCGAATTCA TGGGCCGCTC CGACCAGCAG GTGAAGATTC
```

*FIG. 16 (CONTINUED)*

1151 GCGGTCATCG CATCGAAATC TCCGAAGTGG AGGATGTGCT GTCGCGACTG

1201 CCCGGCGTCC GCGAGGCGGC GGTCGTGGCG CGAGCCGACG CAACCGGAGA

1251 CAAGCGGCTC GTCGCTTATG TCGTCGGCGA GCTCGAGCCG CGGGCGGTGA

1301 AAGAGGCGTT TCGAAGCGAG GCCCCGCACT ATATGACGCC GCATTTCGTC

1351 GTGGCGCTGC AGCGCCTGCC GCGGCTCGAC AATGGCAAGG TCGATCGCAA

1401 GGCGCTTCCC GCGCCGGACG TCGACGCTTT GCTTAGCGAA CGCTATGTCG

1451 CGCCGACGAC CGAGACGGAA GCAGCGATCT GCGCCGTGTT CGCCGAGACG

1501 CTCGGCCTCG CGCGCGTCGG CGCCGACGAC GACTTCTTCG ATCTCGGCGG

1551 CGATTCGATC CGCGCAATTC AGGCGGCGAG CGCGCTGAGA CTGCGAGGAT

1601 ATGAGGCGGC GCCGCGCGAT TTCTTCCAAT ATCCGACCGC AGCGTCTCTC

1651 GCTCCGCGCC TGCGCGTCGC GAAAGACGGG ACGGAGCCGA CTCGCGAGCG

1701 GCGTTCGACG CCCTTCTCTC TCGCCCAGCT CGGCGCAACC GATGTCGAGC

1751 GATTGAAGGC TGTGCATGGT GACGCTCAGG ATATATATCC GCTCACGCCC

1801 ATGCAGGAAG GCATGTTGTT CCATGCGCTC TCGCAGCAGG GGACCGGCCT

1851 CTATCTGATG CAGGACCGCT ACGAGATCAA AGGCGCGCTC GATATCGACG

1901 CCTTCCTAGA AGCGTGGCGG CGCGTTATCG ACCGGCACGA CATTCTACGC

1951 ACCTCCTTCG ACTGGTCGAG CGAAGGACGG CCGCATCAAA TCGTGCATCG

2001 CGCCGCGGCG CTTCCCTTCG AGGTCACGGA TCTGAGCGGA GCCACGGAAC

2051 AGGAGCAGAC GAACGCGATC GATCGCGCGC TCGCCGCCGA AAGGGAAGCG

2101 GGCTTCGACC TCGCGCAGGC GCCGCTCATG CGCATCCGCA TCTTTCGCCT

2151 CGCAGATGAT CGTCACATCT GCGTGCGCAG CTTCCATCAC ATCATATTGG

2201 ACGACTGGTG CACGTCTTTG CTCATCCTCG ACGTTCGCCG GCACTATGCC

2251 GCTGTGCGAA AGGGAGAGGC CACGGAATTT GCGCCGGCGC CGCAGTTCTG

2301 GCGCTATATC GAATGGATCG CGGAACAGAG CGAGCGGACA GCCGAGCAGT

2351 TCTGGCGCGC CCATCTCGAC GGATTCGTCG AGCCGACGCC GCTCGTCGGG

2401 GCGAAACCGT CGACACGCGA CGCCGTCTCC TTCGTCGAGG ATATCGTCGT

2451 CGACCTTTCC AACGAGATGT ACGAGCGGCT CAGAGCGCTC GTTCAGCAAC

2501 GCCGGCTGAC GCTGAACACT TTCGTGCAAG GAGCGCTCGC GCTCACTCTC

FIG. 16 (CONTINUED)

```
2551  GGACGCGCCG GCGGGGTCGA CGATGTCGTC TTCGGCGTCA CCGCGTCCGG
2601  CCGGCCGATC GATCTCGACG GCGCCGACGC GACGCTCGGG CTATTCATCA
2651  ACAGCCTGCC CTTGCGCGTC AGGATCGACC GACGCAAGCC TGTCATCGAT
2701  TGGCTCCGCG AGATTCTCGC GGACAATCTC GAGATGCGCC AATATGAGTT
2751  CGTTCCCCAG ACGAACATCC AGCGCTGGAG CGCCATCTCG CGCTCCGACG
2801  CGCCGCTCTT CCAGCATCTG CTGACCTTCG AGAACGCGCC GCTCGACCCA
2851  TGCCGTGCGA AGGGGAGAAG GAACGTGATC GACATCGATC TGCTGCAGAA
2901  CCAGCCGGGC TGG
```

*mesD* (SEQ ID NO:4):
```
  1  CCGCGGATTT TGACCTGATG ATCGGCGCGG CCGAGATATT GGATGTTCCC
 51  GTCCCGATGA TAGCGCGCCA GATCGCCCGT CCGATAGAGG CGCTCTCCGG
101  GAGCCCCGAA CGGGCTTGGA ACAAATCTCT CCGCCGTGAG GTCGGGGCGG
151  TTCAGATAGC CGCGCGCGAG GCCGGCCCCG CCAATGTAGA GCTCGCCCGA
201  CATGCCAATC GGCAAAAGAT GTAGATTTGA GCCCCGAATA TAGACTTGCA
251  GATCCCTGAG AGGACGCCCG ACGCCCTCTG TTTCATCAGG GCGAATCAAT
301  TGCCGTGTCA CATGCACAGT GGTTTCGGTG ATGCCGTACA TGTTGCAGAG
351  TCGAGGCCGC GTGTGGCCGT GCCGTTCGAA CCACCCCTTC AACCTCTCGA
401  CTTCGAGGGC TTCGCCGCCA AAAATGACCA GCTTCAGCGA CGACAACCCG
451  GCGAGGTGAA TCGAATCGAC AGAGTCGAGA TTGTAGAAGT TGGATGGCGT
501  TTGATTGAGA ACCGTGACGG ATTGCGCGCG TAAAAGCTCG TAGAACGCCT
551  CGGGAGATCG CGAAACCCAA TAGGGTACGA TAATAAGTCT TCCGCCATAG
601  AGGAGCGCGC CCCATATCTC CCAGACAGAA AAGTCGAACG CAAACGAGTG
651  GAACAGCGTC CAGACATCAT CGCAGGAAAA ATCAAACGCC TCTTCGGCGG
701  CTGCAAAGAG CCGGCGAACA TTTTGGTGCG TGACCCCGAC GCCCTTCGGC
751  TTGCCTGTAC TCCCCCACGT GTA
```

*FIG. 16 (CONTINUED)*

USE OF METHANOBACTIN

CROSS-REFERENCE TO RELATED APPLICATIONS

This application is a divisional of U.S. patent application Ser. No. 11/880,886, filed on Jul. 24, 2007, which claims the benefit of the filing date of U.S. Provisional Patent Application Ser. No. 60/833,067, filed on Jul. 24, 2006, which applications are incorporated herein by reference in their entirety.

STATEMENT OF GOVERNMENT RIGHTS

This invention was made with government support under Grant Nos. DE-FG02-96ER20237 and DE-FC26-05NT42431 awarded by the Department of Energy. The government has certain rights in the invention.

BACKGROUND

Methanotrophs are a group of ubiquitous Gram-negative bacteria that utilize methane as their sole source of carbon and energy. There are two enzymes used by methanotrophs to oxidize methane. One enzyme, the particulate methane monooxygenase (pMMO) is found in most known methanotrophs and is located in the cytoplasmic membrane. The other enzyme, the soluble methane monooxygenase (sMMO) is found is some methanotrophs and is located in the cytoplasm. Methanotrophic physiology is strongly affected by the amount of bioavailable copper. In methanotrophs that have both MMOs, copper is known to cause a shift in expression from the sMMO at low copper-to-biomass ratios to pMMO at high copper-to-biomass ratios. Additionally, the amount of pMMO produced increases exponentially with the amount of copper present.

*Methylosinus trichosporium* OB3b is thought to acquire copper by producing a copper chelating chalkophore, methanobactin. Methanobactin (mb) is a low molecular mass (1,154 Da) 7 amino acid chromopeptide observed in both the extracellular and membrane fraction of many, and perhaps all aerobic methanotrophs (DiSpirito, 2004; DiSpirito, 1998; Kim et al., 2004; Tellez et al., 1998; Zahn et al., 1996), which has very high affinity for copper.

When isolated from the membrane fraction, methanobactin contains one copper atom and is predominately associated with pMMO (Zahn et al., 1996; Choi et al., 2005; Choi et al., 2003). In the extracellular fraction, the majority of methanobactin is metal free (DiSpirito et al., 1998; Zahn et al., 1996). This proposed copper-siderophore, or chalkophore role (Kim et al., 2004), is based on copper uptake and localization studies (DiSpirito et al., 1998; Tellez et al., 1998; Zahn et al., 1996; Choi et al., 2005; Morton et al., 2000), chelation of copper in soil systems (Morton et al., 2000), characterization of constitutive sMMO mutants in *Methylosinus trichosporium* OB3b (DiSpirito et al., 1998; Tellez et al., 1998; Fitch et al., 1993; Phelps et al., 1992), and copper-binding studies (DiSpirito et al., Zahn et al., 1996; Choi et al., 2005; Choi et al., 2006; Kim et al., 2005).

The structure of copper containing methanobactin (Cu-methanobactin) following exposure to high copper concentrations shows one methanobactin binds one copper atom in a novel S, and N coordination by the 4-thiocarbonyl-5-hydroxy imidazolate (THI) and 4-hydroxy-5-thiocarbonyl imidazolate (HTI) moieties (Kim et al., 2004). However, spectral, kinetic and thermodynamic studies indicate that initial coordination of Cu(II) and Cu(I) differs from the coordination observed in the crystal structure (Choi et al., 2006). Methanobactin (mb) appears to initially coordinate Cu(II) as tetramer or oligomer by THI and possibly Tyrosine (FIG. 1, reaction 1). This initial coordination is followed by a reduction of Cu(II) to Cu(I) (FIG. 1, reaction 2), and then followed by a change in metal ligation, resulting in coordination by both THI and the HTI (FIG. 1, reaction 3). At Cu(II) to mb ratios above 0.25 the Cu(II) is coordinated as a dimer (FIG. 1, reaction 4), followed by coordination as a monomer at Cu(II) to mb ratios above 0.5 Cu per mb (FIG. 1, reactions 5, 6 and 7).

What is needed is a metal binding system useful in multiple applications.

SUMMARY OF THE INVENTION

The invention provides methods to reduce certain metals with an isolated metal binding biosynthetic molecule and methods of using an isolated metal binding biosynthetic molecule to prepare compositions of metal nanoparticles useful for a variety of manufacturing processes as well as the treatment of certain disorders present in, for example, mammals, such as humans. As described hereinbelow, to examine the physiological role of methanobactin, and to distinguish it from iron binding siderophores, the spectral (UV-visible absorption, circular dichroism, fluorescence, and X-ray photoelectron) and thermodynamic properties of metal binding by methanobactin were examined.

Initial screening by UV-visible absorption spectroscopy showed that mb will bind Cu(II), Cu(I), Ag(I), Au(III), Cd(II), Co(II), Fe(III), Hg(II), Mn(II), Ni(II), Pb(II), U(VI), or Zn(II) but not Ba(II), Ca(II), La(II), Mg(II), and Sr(II). Based on the redox and spectral properties described below, the metals bound by mb were placed into two groups. Choi et al. (2006) recently described the spectral and thermodynamic properties of Cu(II) and Cu(I) which are designated as mb group A metals. As described below, metals that showed a final coordination via 4-thiocarbonyl-5-hydroxy imidazolate (THI), 4-hydroxy-5-thiocarbonyl imidazolate (HTI) and possibly Tyr were placed in group A. In general, mb also reduced these metals without the addition of an external reductant. Lastly, depending on the metal concentration, mb coordinated group A metals as either a tetramer, dimer, or monomer. In addition to Cu, Group A metals include Ag(I) and Au(III), Hg(II), Pb(II) and possibly U(VI).

Group B metals include the transition metals Cd(II), Co(II) Fe(III), Mn(II), Ni(II), and Zn(II). Group B metals were characterized by a final coordination to THI and without a change in the oxidation state of the metal. In addition, depending on the concentration of group B metal, mb coordinated group B metals as either a tetramer or dimer, but generally not as a monomer. Thus, it appears that even in the presence of excess metals, mb coordinates group B metals as a dimer. With respect to the copper binding model proposed by Choi et al. (2006), coordination of group B metals stops after the initial two binding steps (FIG. 1, reactions 1 and 2*).

From both spectral (UV-visible absorption, fluorescence, circular dichroism (CD), X-ray photoelectric, and electron paramagnetic resonance (EPR)), metal binding, and thermodynamic measurements, in the absence of Cu(II) or Cu(I), methanobactin binds Au(I), Au(III), Co(II), Cd(II), Fe(III), Hg(II), Mn(II), Ni(II), Pb(II), U(VI), and Zn(II) (FIGS. 2-11; Tables 1-3). The binding constants of methanobactin for Au(III), Co(II), Cd(II), Fe(III), Hg(II), Mn(II), Ni(II), U(VI), and Zn(II) were less than those observed with Cu(II) (Table 4). With the possible exceptions of Au(III) and Hg(II), the coordination of these metals differs from that observed with Cu(I) or Cu(II). With the exception of Au(III) and possibly Hg(II), and in contrast to Cu(II), none of the non-Cu metals examined were reduced by methanobactin. Moreover, as described below, Au(III) is reduced to Au(0) and remains associated with methanobactin. Thus, methanobactin may be employed as a soluble delivery/extraction system for a variety of metals, including, but not limited to, Au. For instance, methanobactin may be employed as an aurothiolate-type of treatment system, e.g., to deliver Au(0) for treatment of rheumatoid arthritis. An Au(0)-methanobactin complex containing solution may also be applied to surfaces to generate thin gold films or wires, spotting on semiconductor chips, or in the formation of nanoparticles.

The invention thus provides a method to reduce Au(III), for example, Au(III) salts such as $HAuCl_3$, to Au(0). The method includes contacting a composition, e.g., a solution, comprising an amount of Au(III) and an amount of isolated metal binding biosynthetic molecule, e.g., isolated methanobactin, effective to yield a mixture in which at least a portion of the Au(III) is reduced to Au(0). Further provided is a method to reduce Hg(II) to Hg(0) or Hg(I). The method includes contacting a composition comprising an amount of Hg(II) and an amount of isolated methanobactin, to yield a mixture in which the Hg(II) is reduced to Hg(0) or Hg(I). Also provided is a method to reduce and precipitate other metals, including, but not limited to, precious metals, such as rhodium, silver, palladium or platinum.

Also provided is a method to treat a disease, one or more symptoms of which may be prevented, inhibited or treated by metal or metal complex administration. For instance, the invention provides a method to treat rheumatoid arthritis. The method includes administering an effective amount of complexes of Au(0) and a metal binding biosynthetic molecule, e.g., methanobactin, to a mammal, e.g., a canine, feline, bovine, swine, ovine, caprine, equine, rodent (e.g., hamster, rat, mouse or ferret), non-human primate or human.

The invention also provides a pharmaceutical composition comprising the complexes described herein, or a pharmaceutically acceptable salt thereof, in combination with a pharmaceutically acceptable diluent or carrier. Further, the invention provides a pharmaceutical composition comprising the complexes disclosed herein in combination with other known compounds.

Thus, the invention provides compositions for use in medical therapy, optionally in conjunction with other compounds. Accordingly, the complexes of the invention are useful to inhibit or treat disorders including, but not limited to rheumatoid arthritis, and other such diseases such as cancer, including solid and nonsolid tumors. Also provided is the use of the compositions for the manufacture of a medicament to inhibit or treat rheumatoid arthritis or cancer.

As further described herein, methanobactin binds and reduces Au(III) catalytically to Au(0) and yields gold nanoparticles of varying diameters and shapes. For instance, at AU(III) to methanobactin ratios above 1, methanobactin binds and reduces Au(III) catalytically to Au(0) and yields gold nanoparticles. However, at low ratios of Au(III) to methanobactin, methanobactin binds and reduces Au(III) to Au(0) and yields gold nanoparticles of varying diameters and shapes. Methanobactin may reduce at least 2-5 Au(III) to Au(0) on a molar ratio without the addition of a reductant. In the presence of chemical or reducing agent the number of Au(III) reduced is orders of magnitude higher. One to 2 Au(0) atoms remain bound to methanobactin, and the remainder precipitates as nanoparticles. In general, at Au(III) to methanobactin ratios of about 1 to about 3, the average size of the gold nanoparticles is about 11 nm with a range of about 1.0 nm to about 30 nm, as a dispersed product. The gold nanoparticles may be separated from methanobactin by centrifugation, freeze thawing or lower the pH to below 4.0. Methanobactin may also be used to form stable biochelated Cu(I) which is redox stable in aqueous solutions. Methanobactin may also be used to form stable biochelated mercury (which has use, for example, in the medical and environmental areas), as well as stable biochelated forms of other metals.

Therefore, the invention further provides a method to prepare gold nanoparticles. The method includes contacting a composition comprising an amount of Au(III) and an amount of isolated methanobactin effective to yield a composition comprising gold nanoparticles. The nanoparticles may be isolated and optionally purified. The resulting preparation may be employed to form a layer on surfaces, e.g., gold nanoparticles may be deposited onto surfaces of printed circuit boards or carbon tubes/sheets, used to in colloidal suspensions (e.g., paints and other protective coatings), or in cancer detection. For instance, gold nanoparticles can bind antibodies that can also bind to a tumor antigen (once bound to tumors, infrared heating, for example, can be used to destroy the bound cancer cells).

The invention further provides an isolated nucleic acid molecule comprising a nucleic acid sequence comprising one or more methanobactin (mb) biosynthetic genes, a variant or fragment thereof encoding a polypeptide with substantially the same activity, e.g., at least 80%, 85%, 90%, or 95% the activity or the same activity, as a corresponding full length wild type polypeptide. In one embodiment, the isolated nucleic acid segment comprises mesA (e.g., SEQ ID NO:1 which encodes a polypeptide), mesB (e.g., SEQ ID NO:2 which encodes a polypeptide), mesC (e.g., SEQ ID NO:3 which encodes a polypeptide), and mesD (e.g., SEQ ID NO:4 which encodes a polypeptide), or a variant or fragment thereof encoding a polypeptide with substantially the same activity, e.g., at least 80%, 85%, 90%, or 95% the activity, or the same activity, as a corresponding full length wild type polypeptide. Preferably, the nucleic acid molecule comprising the mb biosynthetic genes hybridizes under moderate, or more preferably stringent, hybridization conditions to one of SEQ ID Nos. 1-4 or the complement thereof. Moderate and stringent hybridization conditions are well known to the art, see, for example Sambrook et al. (*Molecular Cloning: A Laboratory Manual*, Cold Spring Harbor Laboratory, Cold Spring Harbor, N.Y. (2001). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS. A variant nucleic acid sequence of the invention has at least about 80%, e.g., 90%, 95%, or 99%, but less than 100%, contiguous nucleic acid sequence identity to a nucleic acid sequence comprising SEQ ID NO:1, SEQ ID NO:2, SEQ ID NO:3, or SEQ ID NO:4.

The invention also provides a variant polypeptide having at least about 80%, e.g., 90%, 95%, or 99%, but less than 100%, contiguous amino acid sequence identity. A variant polypeptide includes a variant polypeptide having at least about 80%, 85%, 90%, 95% or more, the activity of the polypeptide.

Also provided is an expression cassette comprising a nucleic acid sequence comprising a mb biosynthetic gene, a variant or fragment thereof operably linked to a promoter functional in a host cell, as well as host cells comprising an expression cassette of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

µM mb (cell) aqueous solution at 25° C. Binding isotherm of 1.6 mM HAuCl$_4$ (B). The curve fittings for two-site binding algorithm were used.

Figure 15:
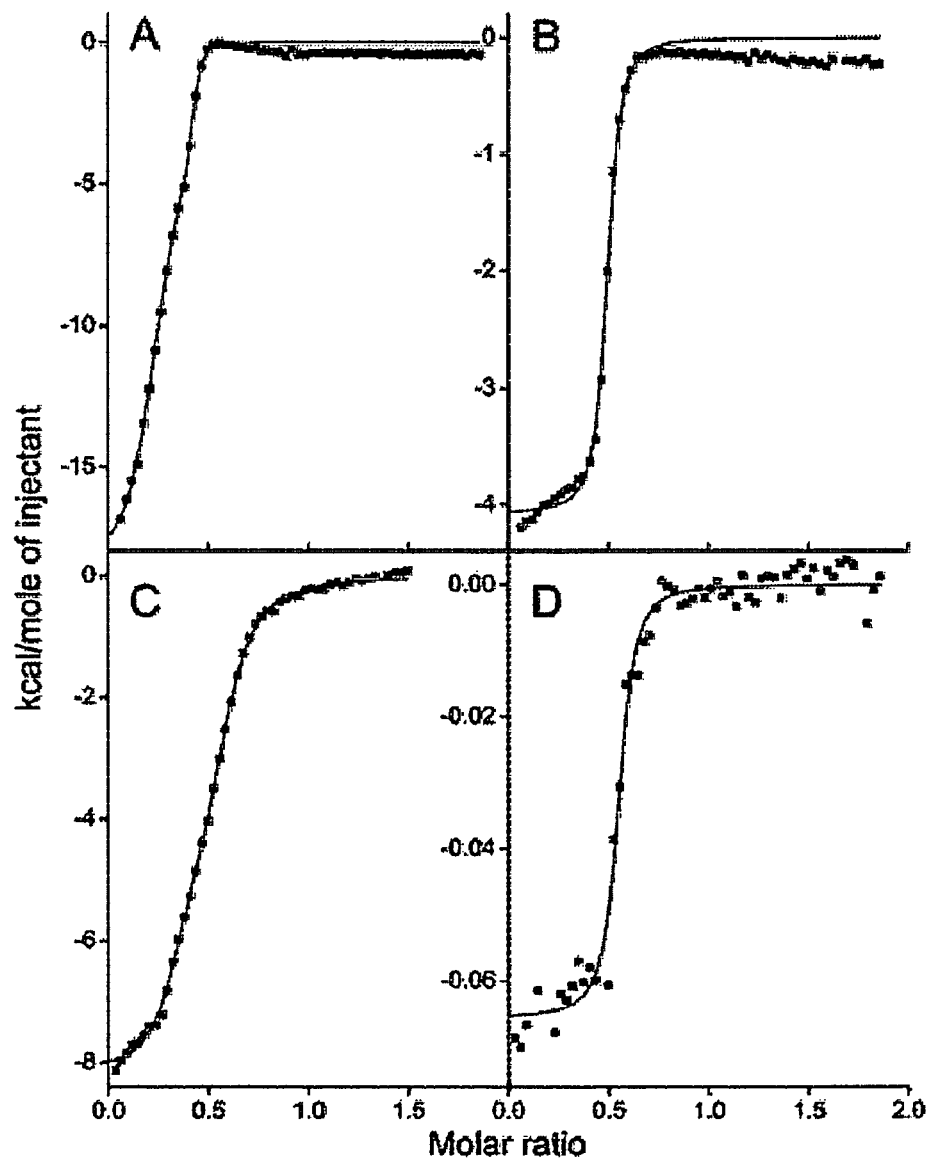

FIG. 15. Binding isotherm of 3.2 mM CdCl$_2$ (A), CoCl$_2$ (B), FeCl$_3$ (C), or MnCl$_2$(D) into 400 mM mb aqueous solution at 25° C. Curve fittings for one-site binding algorithm (B, D) or two-site binding algorithm (A, C) were used.

FIG. 16: Non-ribosomal peptide synthetase genes involved in methanobactin production (mesA, mesB, mesC, mesD; SEQ ID NOs:1-4). At least one open reading frame in SEQ ID NO:1 or its complement encodes a polypeptide which has at least one domain of a mb peptide synthetase, at least one open reading frame in SEQ ID NO:2 or its complement encodes a polypeptide which has at least one domain of a mb peptide synthetase, at least one open reading frame in SEQ ID NO:3 or its complement encodes a polypeptide which has at least one domain of a mb peptide synthetase, and at least one open reading frame in the complement of SEQ ID NO:4 or its complement encodes a polypeptide which has at least one domain of a mb peptide synthetase.

DETAILED DESCRIPTION OF THE INVENTION

Definitions

As used herein, the terms "isolated and/or purified" refer to in vitro preparation, isolation and/or purification of a metal, metal complex, polypeptide, or other biosynthetic product, e.g., methanobactin, or nucleic acid, such as one encoding a methanobactin synthetase, from its natural environment, and from association with other components that is naturally associated with, e.g., components of a cell. For example, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxyribonucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. An oligonucleotide can include a label for detection, if desired.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

As used herein, "chimeric" means that a vector comprises DNA from at least two different species, or comprises DNA from the same species, which is linked or associated in a manner which does not occur in the "native" or wild type of the species.

The term "isolated polypeptide" means a polypeptide encoded by DNA or RNA, synthesized by a synthetase, is synthetic in origin, or some combination thereof, which (1) is not associated with proteins or other cellular components found in nature, (2) is free of proteins or other gene products from the same source, (3) is expressed by a cell from a different species, or (4) does not occur in nature.

The term "sequence homology" means the proportion of base matches between two nucleic acid sequences or the proportion amino acid matches between two amino acid sequences or two sequences having residues at least 50% of which are naturally occurring amino acid residues. When sequence homology is expressed as a percentage, e.g., 50%, the percentage denotes the proportion of matches over the length of sequence from an amino acid containing molecule such as methanobactin or methanobactin synthetase that is compared to some other sequence. Gaps (in either of the two sequences) are permitted to maximize matching; gap lengths of 15 bases or less are usually used, 6 bases or less are preferred with 2 bases or less more preferred.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences are homologous, as this term is used herein, if they have an alignment score of at more than 5 (in standard deviation units) using the program ALIGN with the mutation data matrix and a gap penalty of 6 or greater. See Dayhoff, 1972. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, or molecules having a plurality of amino acids linked via a peptide bond and non-amino acid moieties, the term "substantial identity" means that two sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, "substantially pure" means an object species is the predominant species present (i.e., it is more abundant than any other individual species in the composition), and preferably a substantially purified fraction is a composition wherein the object species comprises at least about 50 percent (e.g., on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

"Therapeutically effective amount" is intended to include an amount of a compound or complex useful in the present invention or an amount of a combination of compounds or complexes, e.g., to treat or prevent a disease or disorder, or to treat the symptoms of a disease or disorder, in a host. A combination of compounds or complexes is preferably a synergistic combination. Synergy, as described for example by Chou and Talalay (1984), occurs when the effect of the compounds, complexes or any combination thereof, when administered in combination is greater than the additive effect of the compounds or complexes when administered alone as a single agent. In general, a synergistic effect is most clearly demonstrated at suboptimal concentrations of the compounds and/or complexes. Synergy can be in terms of lower cytotoxicity, increased activity, or some other beneficial effect of the combination compared with the individual components.

As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

As used herein, the term "patient" refers to organisms to be treated by the methods of the present invention. Such organisms include, but are not limited to, mammals such as humans.

Methods of the Invention

The structural similarities of methanobactin to siderophores in the pyroverdin class (Braum et al., 1999; Crosa et al., 2002; Di Lorenzo et al., 2004; Neilands, 1995) suggested that methanobactin may prove to be a siderophore with a capacity to bind Cu(II) as well as Fe(III). Several other observations suggested that methanobactin may be involved in the mobilization of non-cuprous metals. For example, the coupled increase in iron uptake with increased copper uptake, or copper-induced iron uptake, suggest that methanobactin may be involved in iron uptake (Zahn et al., 1996; Nguyen et al., 1998). Given that methanobactin is the major if not sole extracellular metal binding compound produced by *Ms. tri-*

*chosporium* OB3b (DiSpirito et al., 1998; Choi et al., 2005 Choi et al., 2006; Kim et al., 2005) and the observation by Jenkins et al. (1994) that this bacterium mobilizes Cd(II) in soil columns, methanobactin may bind Cd(II) or other metals. Thus, methanobactin and related molecules may be employed to deliver or modify metals.

In one embodiment, the invention provides for methods which employ a metal binding biosynthetic molecule, i.e., one which is synthesized by one or more gene products, e.g., methanobactin. In one embodiment, the metal binding biosynthetic molecule is methanobactin, or a variant or derivative of methanobactin which binds and reduces metals. In one embodiment, the metal is Au(III). Thus, the invention provides a method to reduce Au(III) which employs a metal binding biosynthetic molecule such as methanobactin. Also provided is a method to prepare complexes of Au(0) and a metal binding biosynthetic molecule such as methanobactin. Further provided is a composition comprising isolated complexes of Au(0) and methanobactin. These isolated complexes may be employed as a soluble delivery system for Au(0), e.g., as a drug, or in the formation of thin gold films or wires and in particular as a selective coating of surfaces. For instance, methanobactin may be used as an aurothiolate-type (gold-sulfur ligand system) in the management of rheumatoid arthritis. Methods of using gold based compounds to treat arthritis are known to the art, see, e.g., Van Roon et al. (2005) and Hamilton et al. (2001). An advantage of using methanobactin as an in vivo delivery vehicle is that it maintains gold in the zero oxidation state, which avoids the toxic effects associated with the oxidation of Au(I) to Au(III).

Also, soluble methanobactin reduces Au(III) to Au(0) at mole ratios >1, to provide particle sizes from about 1 nm to about 85 nm, e.g., about 1.5 nm to about 50 nm, depending on the gold to methanobactin ratio. Average particle size can be 11±4 nm and in one embodiment is a dispersed product (a dispersion).

In the recovery of gold from ores, methanobactin may replace cyanide as a method of gold complexation and solublization. The advantages of methanobactin over cyanide includes its nontoxic nature. Moreover, methanobactin may be used to initially solubilize the gold followed by precipitation at higher gold to methanobactin ratios.

Methanobactin, variants and derivatives thereof may be prepared as described below.

Methods to Isolate Methanobactin from Nonrecombinant Cells

Methods to isolate methanobactin from cells are described in Choi et al. (2005), the disclosure of which is incorporated by reference herein. For instance, *Methylosinus trichosporium* OB3b$^T$ and *Methylococcus capsulatus* Bath are cultured for methanobactin isolation in nitrate minimal salts (NMS) medium containing 0, 0.2 or 1 μM added CuSO$_4$ as described in Choi et al. (2003). The initial copper concentration in NMS medium with no added CuSO$_4$ is 0.29±0.04 μM. The cultures are grown in batch mode to an OD$_{600}$ between 0.7 and 1.2 prior to harvesting for methanobactin. When the OD$_{600}$ reaches the desired level, 80% of the fermenter is harvested and replaced with fresh NMS medium. *Methylococcus capsulatus* Bath is also cultured in NMS medium that contained a final CuSO$_4$ concentration of either 60 or 80 μM as described in Choi et al. (2003). Washed membranes from *Methylococcus capsulatus* Bath are isolated under anaerobic conditions as described by Choi et al. (2003).

Cu-methanobactin and methanobactin are prepared from the spent medium of *Methylosinus trichosporium* OB3b$^T$ or *Methylococcus capsulatus* Bath. For each harvest, the spent medium is centrifuged twice at 9000 g for 20 minutes to remove residual cells. At this stage, the spent medium is either loaded onto a 7×20 cm Dianion HP-20 column (Supelco) or stabilized by the addition of copper as described by Kim et al. (2004), except that the final concentration of added copper is reduced from 10 to 1 mM. The Dianion HP-20 column is washed with two column volumes of H$_2$O, eluted with 60% methanol: 40% water (v/v) and lyophilized. At this stage of purification, methanobactin represents >97% of the material absorbing at 214 or 280 nm and no other chromophores with absorption maxima above 280 nm are present. Purity of methanobactin samples is checked at this stage by HPLC, matrix-assisted laser desorption ionization-time-of-flight (MALDI-TOF) mass spectrometry and UV-visible absorption spectra. Selected samples are purified further by reverse-phase HPLC on a Beckman Gold HPLC system by using a SupelcoSil LC-18 (25 cm×4.6 mm, 5 μm) column at a flow rate of 1.0 ml min$^{-1}$, with 10 mM sodium phosphate buffer, pH 6.6 (solvent A) and 80% acetonitrile/H$_2$O (solvent B) as the mobile phase. A linear gradient consisting of an initial solvent B concentration of 5% following injection to 35% solvent B at 50 minutes and 100% at 55 minutes is used in this purification step.

Sample purity and metal content of final samples were based on the UV-visible absorption spectra, on metal analysis and on molecular masses as determined by MALDI-TOF MS, of the fractions before and after separation by reverse-phase HPLC.

Sources of Nucleic Acid Molecules Useful to Prepare Recombinant Methanobactin

Sources of nucleotide sequences from which nucleic acid molecules encoding a methanobactin synthetase, a variant thereof, or the nucleic acid complement thereof, include RNA, DNA, or a genomic library from any cellular source from which methanobactin can be isolated.

A nucleic acid molecule encoding a methanobactin synthetase can be identified and isolated using standard methods, as described by Sambrook et al. (1989). For example, reverse-transcriptase PCR(RT-PCR) can be employed to isolate and clone methanobactin synthetase DNAs.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al. (1987); Erlich, (1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison. One primer is prepared which is predicted to anneal to the antisense strand, and another primer prepared which is predicted to anneal to the sense strand, of a DNA molecule which encodes a methanobactin synthetase.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone DNAs which encode a methanobactin synthetase is to screen a DNA library. Screening for DNA fragments that encode all or a portion of a DNA encoding a methanobactin synthetase can be accomplished by probing the library with a probe which has sequences that are highly conserved between genes believed to be related to the methanobactin synthetase, e.g., the homolog of a particular methanobactin synthetase from a different species, or by screening of plaques for binding to antibodies that specifically recognize the methanobactin synthetase. DNA fragments that bind to a probe having sequences which are related to the methanobactin synthetase, or which are immunoreactive with antibodies to the methanobactin synthetase, can be subcloned into a suitable vector and sequenced and/or used as probes to identify other cDNAs encoding all or a portion of the methanobactin synthetase.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA.

Nucleic acid molecules encoding amino acid sequence variants of a methanobactin synthetase are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the methanobactin synthetase.

Oligonucleotide-mediated mutagenesis is a preferred method for preparing amino acid substitution variants of a methanobactin synthetase. This technique is well known in the art as described by Adelman et al. (1983). Briefly, methanobactin synthetase DNA is altered by hybridizing an oligonucleotide encoding the desired mutation to a DNA template, where the template is the single-stranded form of a plasmid or bacteriophage containing the unaltered or native DNA sequence of the methanobactin synthetase. After hybridization, a DNA polymerase is used to synthesize an entire second complementary strand of the template that will thus incorporate the oligonucleotide primer, and will code for the selected alteration in the methanobactin synthetase DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13 mp18 and M13 mp19 vectors are suitable), or those vectors that contain a single-stranded phage origin of replication. Thus, the DNA that is to be mutated may be inserted into one of these vectors to generate single-stranded template. Production of the single-stranded template is described in Sections 4.21-4.41 of Sambrook et al. (1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the methanobactin synthetase, and the other strand (the original template) encodes the native, unaltered sequence of the methanobactin synthetase. This heteroduplex molecule is then transformed into a suitable host cell, usually a prokaryote such as $E.\ coli$ JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as $E.\ coli$ JM101.

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding a methanobactin synthetase is typically a "sense" DNA sequence cloned into a cassette in the opposite orientation (i.e., 3N to 5N rather than 5N to 3N). Generally, the preselected DNA sequence or segment is in the form of chimeric DNA, such as plasmid DNA, that can also contain coding regions flanked by control sequences which promote the expression of the preselected DNA present in the resultant cell line.

Aside from preselected DNA sequences that serve as transcription units for a methanobactin synthetase, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters are known to the art. Other elements functional in eukaryotic host cells, such as introns, enhancers, polyadenylation sequences and the like, may also be a part of the preselected DNA. Such elements may or may not be necessary for the function of the DNA, but may provide improved expression of the DNA by affecting transcription, stability of the RNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Additional reporter genes include those which code for green, yellow or red fluorescent proteins. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al. (1989), provides suitable methods of construction.

The recombinant DNA can be readily introduced into the host cells, e.g., mammalian, bacterial, yeast or insect cells by transfection with an expression vector comprising DNA encoding a methanobactin synthetase or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell. Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular methanobactin synthetase, e.g., by immunological means (ELISAs and Western blots) or its product.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

Isolated Methanobactin and its Synthetase, and Variants and Derivatives Thereof The present isolated methanobactin, methanobactin synthetase, or variants of derivatives thereof, can be synthesized in vitro, e.g., by the solid phase peptide synthetic method, by recombinant DNA approaches (see above), or for wild-type methanobactin or methanobactin synthetase, isolated from nonrecombinant cells (see above). A variant may include amino acid residues not present in a corresponding native methanobactin or methanobactin synthetase, and/or internal deletions relative to the corresponding native methanobactin or methanobactin synthetase, and may include at least one D-amino acid. Methanobactin or methanobactin variants, methanobactin synthetase or methanobactin synthetase variants which are subjected to chemical modifications, such as esterification, amidation, reduction, protection and the like, are referred to as "derivatives."

The solid phase peptide synthetic method is an established and widely used method, which is described in the following references: Stewart et al. (1969); Merrifield (1963); Meienhofer (1973); Bavaay and Merrifield (1980); and Clark-Lewis et al. (1997). After synthesis methanobactin, a variant thereof, or a derivative thereof can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given methanobactin or methanobactin synthetase can be readily prepared. For example, amides of the variants of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the methanobactin or methanobactin synthetase, or variant thereof. Other amino-terminal modifications include aminooxypentane modifications.

The amino acid sequence of a methanobactin or methanobactin synthetase can be modified so as to result in a methanobactin or methanobactin synthetase variant. The modification includes the substitution of at least one amino acid residue for another amino acid residue, including substitutions which utilize the D rather than L form, as well as other well known amino acid analogs, e.g., unnatural amino acids such as α,α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids, imino acids, tert-butylglycine, and may include THI and HTI.

One or more of the residues of methanobactin or methanobactin synthetase can be altered, so long as the variant is biologically active. For example, it is preferred that the variant has at least about 10%, e.g., 50%, 60%, 70%, 80%, 90% or more of the biological activity of the corresponding non-variant methanobactin or methanobactin synthetase. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide can readily be determined by assaying the specific activity of the peptide variant. Assays are described in detail herein.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions variants with non-conservative substitutions. Non-conservative substitutions entail exchanging a member of one of the classes described above for another.

Acid addition salts of the protein or variant or of amino residues of the protein or variant may be prepared by contacting the protein or amine with one or more equivalents of the desired inorganic or organic acid, such as, for example, hydrochloric acid. Esters of carboxyl groups may also be prepared by any of the usual methods known in the art.

Exemplary methanobactin variants include: $X_0$-Met-$X_1$-$X_1$-hydroxy thiocarbonyl imidazolate-pyrrolidine-Tyr-$X_1$-$X_1$-$X_2$-hydroxy thiocarbonyl imidazolate-$X_3$, wherein $X_0$ is absent, one or more amino acids, e.g., a tag useful for purification or isolation, or other small molecule; $X_1$ is Cys, Ser, or Thr; $X_2$ is any amino acid; and $X_3$ is absent, an isopropylester, one or more amino acids, e.g., a tag useful for purification or isolation, or other small molecule.

Dosages, Formulations and Routes of Administration of the Metal Complexes of the Invention The amount of complex administered is selected to treat a particular indication. The amount complexes of the invention administered will vary depending on various factors including, but not limited to, the disease, whether prevention or treatment is to be achieved.

Administration of the complexes in accordance with the present invention may be continuous or intermittent, depending, for example, upon the recipient's physiological condition, whether the purpose of the administration is therapeutic or prophylactic, and other factors known to skilled practitioners. The administration of the complexes of the invention may be essentially continuous over a preselected period of time or may be in a series of spaced doses. Both local and systemic administration is contemplated.

One or more suitable unit dosage forms comprising the complexes of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the complex with liquid carriers, solid matrices, semi-solid carriers, finely divided solid carriers or combinations thereof, and then, if necessary, introducing or shaping the product into the desired delivery system.

When the complexes of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Formulations suitable for vaginal administration may be presented as pessaries, tampons, creams, gels, pastes, douches, lubricants, foams or sprays containing, in addition to the active ingredient, such carriers as are known in the art to be appropriate. Formulations suitable for rectal administration may be presented as suppositories.

Pharmaceutical formulations containing the complexes of the invention can be prepared by procedures known in the art using well known and readily available ingredients. For example, the complex can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the complexes of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The complexes of the invention can also be formulated as elixirs or solutions for convenient oral administration or as solutions appropriate for parenteral administration, for instance by intramuscular, subcutaneous or intravenous routes.

The pharmaceutical formulations of the complexes of the invention can also take the form of an aqueous or anhydrous solution or dispersion, or alternatively the form of an emulsion or suspension.

Thus, the complex may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

For administration to the upper (nasal) or lower respiratory tract by inhalation, the complexes of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the complex may be administered via nose drops, a liquid spray, such as via a plastic bottle atomizer or metered-dose inhaler. Typical of atomizers are the Mistometer (Wintrop) and the Medihaler (Riker).

The local delivery of the complexes of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the complexes may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of an agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The complex may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents, or preservatives. Furthermore, the active ingredients may also be used in combination with other agents, for example, oral contraceptives, bronchodilators, anti-viral agents, steroids and the like.

The invention will be further described by the following non-limiting examples.

Example 1

Preparation of Methanobactin

A non-ribosomal peptide synthetase (NRPS) gene from *M. trichosporium* OB3b was cloned because a potential NRPS, MCA2107, from *Methylococcus capsulatus* Bath was suggested as the gene for synthesis of a methanobactin-like copper chelating peptide (Ward et al., *PLoS Biol.*, 2:e303 (2004)). The NRPS genes from *M. trichosporium* OB3b were originally located by using degenerate PCR primers designed from the conserved regions of the protein sequence of MCA2107. The products of these PCR reactions were sequenced and the sequences were extended using the GenomeWalker kit from BD Biosciences (San Jose, Calif.). RT-PCR employed specific primers for each of the 3 potential NRPSs. *M. trichosporium* OB3b was then grown either with 10 mM $CuSO_4$ or in the complete absence of copper, and total RNA was extracted. DNA was removed from the RNA by a reaction with DNAse. Reverse transcription and PCR were done in the same tube with Invitrogen's (Carlsbad, Calif.) One-step RT-PCR kit according to the manufacturer's directions.

Results

Identification of 3 Potential Non-Ribosomal Peptide Synthetase Genes.

The non-ribosomal peptide synthetases (NRPS) genes mesA, B, C and D (FIG. 16; SEQ ID NOs:1-4) all had a high degree of homology to other NRPSs in the NCBI protein database. mesA is 59% and 72% identical and positive to an NRPS amino acid adenylation sequence from *Anabaena variabilis*, mesB is 51% and 65% identical and positive to a peptide synthetase NRPS from *Anabaena circinalis*, and mesC is 38% and 52% identical and positive to an amino acid adenylation NRPS from a *Bradyrhizobium* species, and mesD is 63% and 75% identical and positive to an amino acid adenylation sequence from *Anabaena variabilis*. MesA appears to be at least 1.6 kb and encodes an about 533 amino acid protein, mesB is at least 2.34 kb and encodes an about 742 amino acid protein, and mesC is at least 2.9 kb and encodes an about least 959 amino acid protein, and mesD is at least 0.8 kb and encodes an about 258 amino acid protein.

Measurement of Methanobactin and mesC Gene Expression in *M. trichosporium* OB3b.

The expression of the NRPS increased with an increase in copper in the medium, implying a positive feedback mechanism. This fits well with the data on the presence of methanobactin in the media. It was at a maximum when the cells are still using the sMMO as the primary methane oxidation enzyme, and was quickly depleted from the media as the cells move to pMMO for methane oxidation. The likely reason why there is little methanobactin in the media at 10 mM $CuSO_4$ is that all of the methanobactin is binding to copper and is being reabsorbed into the cells, even though it is being created at a faster rate.

UV/VIS Spectrophotometry of Methanobactin Bound to a Range of Metals.

The spectrographic characteristics of methanobactin change as it binds to different metals. Of particular note is the relatively strong change with binding to zinc and mercury, implying relatively strong binding.

Discussion

It is possible that methanobactin is synthesized via a non-ribosomal peptide synthetase (NRPS) because of its small size and the inclusion of multiple nonstandard amino acids in its structure. The 3 NRPS's described above may be the gene or genes responsible for the synthesis of methanobactin.

Example 2

Metal Binding by Methanobactin

To determine if methanobactin can function as a siderophore and/or to mobilize metals other than copper, the metal binding properties of methanobactin were examined. In particular, the spectral and thermodynamic properties of Ag(I), Au(III), Co(II), Cd(II), Fe(III), Fe(II), Hg(II), Mn(II), Ni(II), Pb(II) U(VI), and Zn(II) binding were examined. The results suggest that methanobactin is primarily involved copper mobilization, but the binding of different metals by methanobactin suggests that methanotrophic activity may also play a role in solubilization of many metals in situ.

Some examples of metals which methanobactin can lower the oxidation states and/or chelate are given below. Chelation may increase the solubility of the metals (especially important for inducing excretion of toxic metals). Lowering the oxidation state can also change the solubility, or cause the formation of nanoparticles of any of these metals.

| | Precious Metals | Oxidation States | |
|---|---|---|---|
| Environmental Contaminates | Gold | 1, 3 | Used in jewelry and coinage, soluble or nanoparticle gold has medical applications. Used in electrical connections to avoid corrosion. |
| | Rhodium | 2, 3, 4 | Alloying agent for hardening platinum and palladium |
| | Silver | 1 | Used in photography and jewelry |
| | Palladium | 1 | Catalyst for hydrogenation/dehydrogenation reactions |
| | Platinum | 2, 3, 4 | Catalyst is catalytic converters and fuel cells, also in jewelry |
| | Iridium | 2, 3, 4, 6 | Alloying agent for hardening platinum |
| | Uranium | 4, 6 | Primary starting material in nuclear reactors |
| | Strontium | 2 | Common radioactive pollutant in nuclear fallout |
| | Technetium | 2, 4, 5, 6, 7 | Abundant in nuclear waste. Product of Uranium decay. |
| | Plutonium | 3, 4, 5, 6 | Fissile component of nuclear weapons |
| | Cesium | 1 | Found in nuclear waste |
| | Thorium | 4 | Byproduct of Uranium fission. Present in nuclear waste |
| Medically Relevant Toxic Metals | Chromium | 2, 3, 6 | Used in paints and dyes |
| | Lead | 2, 4 | Poisonous metal used in paints, weights, and solder for electronics |
| | Arsenic | −3, 3, 5 | Poisonous metal present in treated lumber and some insecticides |
| | Selenium | −2, 2, 4, 6 | Toxic at high doses, sometimes present in agricultural runoff |
| | Mercury | 1, 2 | Poisonous metal found in thermometers and barometers |
| | Cadmium | 2 | Acuity toxic to the liver and kidney, also carcinogenic. Can be found in Ni-Cd batteries, and silver solder |
| | Cobalt | 2, 3 | Commonly used in metal alloys, and pigments. Toxic at high concentrations |

Materials and Methods

Organisms, Culture Conditions, and Isolation of Methanobactin.

*Ms. trichosporium* OB3b was cultured in either 0 or 0.2 μM $CuSO_4$ amended nitrate minimal salts (NMS) medium as previously described (Choi et al., 2005). Mb was prepared from *Ms. trichosporium* OB3b as described previously (Choi et al., 2005, Choi et al., 2006), except the rotary evaporation treatment was removed from the isolation procedure. Instead the methanol was removed during lyophilization. For preparations of metal saturated methanobactin samples, $CdCl_2$, $CoCl_2$, $FeCl_3$, $MgCl_2$, $MnCl_2$, $NiCl_2$, or $ZnSO_4$ was added to the spent media to a final concentration of 2 mM followed by 8 hours incubation in the dark at 4° C. The spent medium was then centrifuged twice at 15,000×g for 20 minutes to remove metal precipitations and loaded on a 7×20 cm Dianion HP-20 column (Supelco, Bellefonte, Pa.). Bound metal-methanobactin were washed with 4 column volumes of $H_2O$ and eluted with 60% methanol:40% $H_2O$ and lyophilized. Due to precipitation or altered column binding properties following exposure to excess metal concentrations, the concentration of Au(III), Fe(III), Hg(II), and U(IV) bound by mb were determined via titration experiments (see below).

Metal Titrations.

Metal titration experiments were determined by addition of 100 µM, 1 mM, or 10 mM solutions of $AgNO_3$, $HAuCl_4$, $CdCl_2$, $CoCl_2$, $CrO_3$, $CuSO_4$, $FeCl_3$, $HgCl_2$, $MgCl_2$, $MnCl_2$, $NiCl_2$, $Pb(NO_3)_2$, $UO_2(NO_3)_2$, or $ZnSO_4$ to 50 µM methanobactin dissolved in $H_2O$, pH 6.8 as previously described for Cu(II) or Cu(I) titrations (Choi et al., 2006) unless otherwise stated. Glassware was soaked in 0.1 N $HNO_3$ for 12 hours then rinsed with milliQ $H_2O$. For the metal replacement experiments, 50 µM aqueous mb solutions were preloaded with equimolar of $AgNO_3$, $HAuCl_4$, $CaCl_2$, $CdCl_2$, $CoCl_2$, $CrO_3$, $CuSO_4$, $FeCl_3$, $HgCl_2$, $MgCl_2$, $MnCl_2$, $NiCl_2$, $Pb(NO_3)_2$, $UO_2(NO_3)_2$, or $ZnSO_4$, incubated for 10 minutes followed by the addition of equimolar $CuSO_4$ then monitored via UV-visible absorption spectroscopy every 30 seconds for 0.5-120 minutes. Between scans the samples were stored in the dark to avoid photodegradation (Choi et al., 2005).

Spectroscopy, Isothermal Titration Calorimetry (ITC), and Metal Determinations.

UV-visible absorption, florescence spectra, circular dichroism (CD), and metal determinations via inductively coupled plasma atomic emission-mass spectroscopy (ICP-MS) were determined as previously described (Choi et al., 2003; Choi et al., 2006). In contrast to a previous report (Choi et al., 2006), the base line was used as a reference point of 0 instead of isosbestic point e for the comparison of Δes.

CD spectra measurements were carried out on either a JASCO J-710 spectropolarimeter (Jasco Co, Tokyo, Japan) or on a Applied Photophysics SX.18MV CD spectrophotometer as previously described (Choi et al., 2006)). Metals were titrated into 100 µM aqueous mb solution.

EPR samples were prepared by adding equimolar metals to 5 mM mb aqueous solutions. After 5 minutes of incubation, samples were transferred to a quartz EPR tubes, then frozen in a liquid nitrogen bath, and the spectra determined as previously described (Choi et al., 2006)).

ITC was performed with following modifications from the previously described procedure (Choi et al., 2006). First, concentrations of the titrant and cell solutions were raised to 3.2 mM and 0.4 mM, respectively. Second, the interval between titrant injections were decreased to 600 s and the stirring rate decreased to 380 rpm.

X-ray Photoelectron Spectroscopy (XPS).

XPS was preformed on a model Phoibos-150 hemispherical analyzer (SPECS Scientific Instruments, Sarasota, Fla.) or on a model 5600ci spectrophotometer (Perkin-Elmer Inc., Eden Prairie, Minn.) as previously described (Choi et al., 2006).

Transmission Electron Microscroscopy.

Gold nanoparticle production was determined by addition of 10 mM aqueous solutions of $HAuCl_4$ to 1 or 5 mM aqueous mb solutions. Mb solutions were prepared freshly and immediately dispensed into 1.8 ml glass vials. Gold solutions were added to the glass vials containing mb solutions with a final molar ratio of 0, 0.1, 0.2, 0.4, 0.75, 1.0, 1.5, 2.0, 3.0, 4.0, 5.0, 10.0 15.0 or 20.0 Au(III) to mb. All samples were incubated for 15 minutes with or without stirring. In some cases the Au-mb solutions were spotted on formvar-coated Ni or Cu grids. Other samples were subjected to one freeze thaw cycle before spotting on formvar-coated Ni or Cu grids. Lastly some samples were centrifuged at 10,000 g for 2 minutes at room temperature and the loose red pellet spotted on formvar-coated Ni grids. The samples on Ni or Cu grids were then dried under vacuum and examined with a JEOL 1200× scanning/transmission electron microscope.

Results

Metal Bound by Mb and Metal Binding Groups

Initial screening by UV-visible absorption spectroscopy showed that in the absence of Cu(II) or Cu(I), mb will bind Ag(I), Au(III), Cd(II), Co(II), Fe(III), Hg(II), Mn(II), Ni(II), Pb(II), U(VI), or Zn(II), but not Ba(II), Cr(VI), La(III), Mg(II), or Sr(II) (see below). Based on the redox and spectral properties described below, the metals bound by mb were placed into two groups. Choi et al. (2006) recently described the spectral and thermodynamic properties of Cu(II) and Cu(I) which are designated in mb group A metals. Metals that showed a final coordination via 4-thiocarbonyl-5-hydroxy imidazolate (THI), 4-hydroxy-5-thiocarbonyl imidazolate (HTI) and possibly Tyr were placed in group A. In general, mb also reduced these metals without the addition of an external reductant. Lastly, depending on the metal concentration, mb coordinated group A metals as either a tetramer, dimer, or monomer. In addition to Cu, Group A metals include Ag(I) and Au(III), Hg(II), Pb(II) and possibly U(VI).

Figure 1:
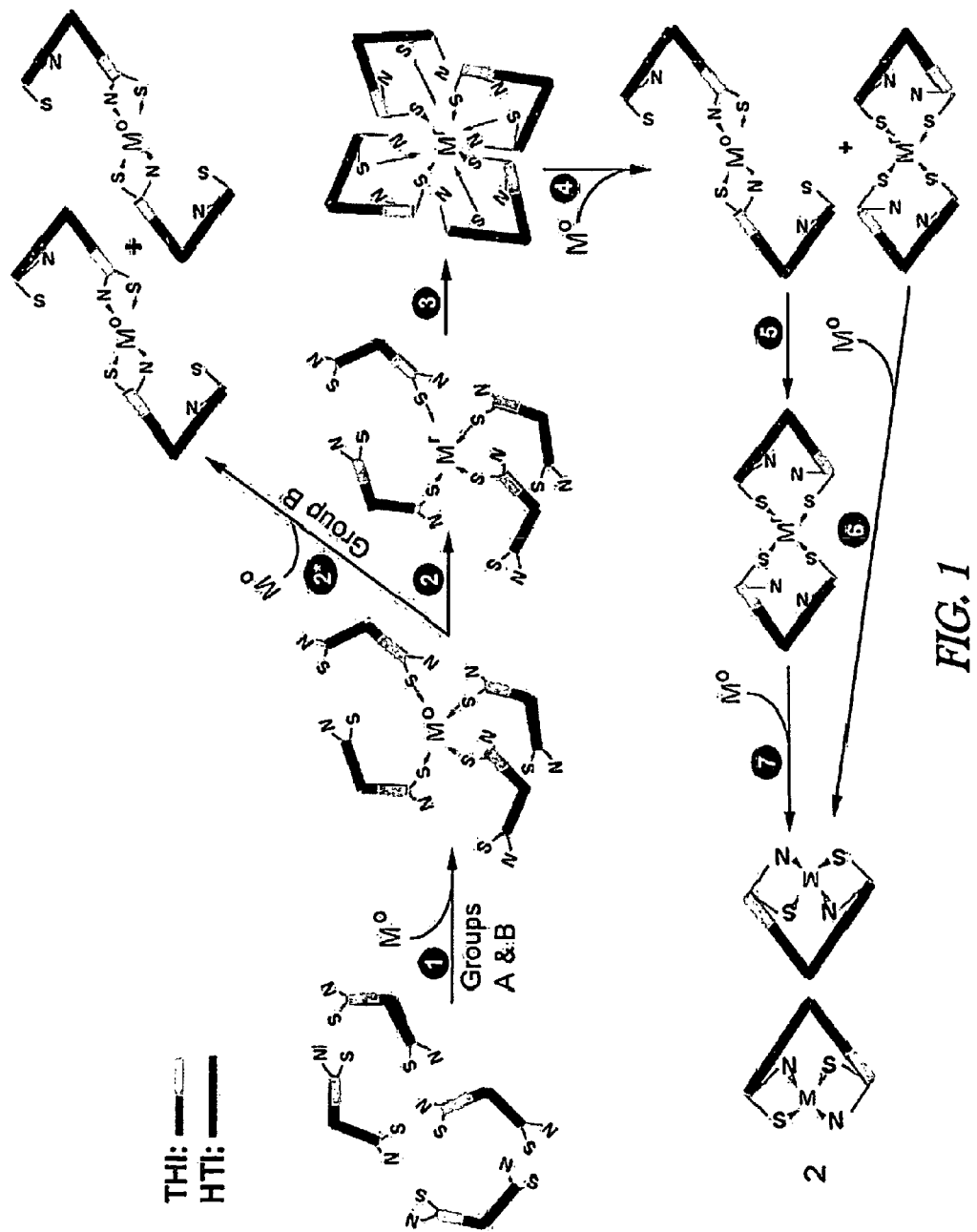
FIG. 1. Model for the binding of group A (Ag(I), Au(III), Cu(II), Hg(II), Pb(II), and (U(IV)), group B (Cd(II), Co(II), Fe(III), Ni(II), Mn(II) and Zn(II) metals by methanobactin. Methanobactin is represented as two bars ending in the $N^\epsilon$ atom of each imidazolate and the S atom of each thiocarbonyl group on 4-thiocarbonyl-5-hydroxy imidazolate (THI; yellow and orange bar) and 4-hydroxy-5-thiocarbonyl imidazolate (HTI; orange bar)). Abbreviations: $M^o$, metal in the oxidation state added to mb solutions and $M^r$, metal reduced by mb.

Group B metals consist of the transition metals Cd(II), Co(II), Fe(III), Mn(II), Ni(II), and Zn(II). Group B metals were characterized by a final coordination to THI and without a change in the oxidation state of the metal. In addition, depending on the concentration of group B metal, mb coordinated group B metals as either a tetramer or dimer, but not as a monomer. Thus, even in the presence of excess metals, mb coordinates group B metals as a dimer. With respect to the copper binding model proposed by Choi et al., coordination of group B metals stops after the initial two binding step (FIG. 1, reactions 1 and 2*).

UV-Visible Absorption Spectra

Group A Metals

As observed with copper (Choi et al., 2006), the binding of Au(III) (FIGS. 2A & 2B), Ag(I) (FIGS. 3A & 3B) and U(VI) (results not shown) resulted in a decreased absorption at 394 nm suggesting coordination to THI (Table 1). In addition to a decrease in absorption at 394 nm, the addition of Hg(II) or Pb(II) also resulted in a shift in the absorption maxima to 385 and 400 nm, respectively (results not shown). Spectral changes were also observed at 340 nm following the addition of group A suggesting coordination to HTI. However, in contrast to Cu(I), Cu(II) and U(VI) which showed a decreased absorbance at 340 nm following metal binding (Choi et al., 2006), the spectral changes associated with HTI following of other group A metals were complex. At Au(III) or Hg(II) concentrations ≤0.3 metal per mb, a red shift in the absorption maximum from 340 to 363 nm was observed with an increased absorption at 363 nm (FIGS. 2A and 2B). At Au(III) or Hg(II) concentrations >0.3 metal per mb, a decrease in absorbance at 363 nm was observed. A similar response to metal concentration was observed at 302 nm, where an increase in absorbance occurred at low metal concentrations (i.e., ≤0.3 metal per mb) followed by a decreased absorbance at metal to mb ratios between 0.3 and 1.0 metal per mb and an increased absorbance at metal to mb concentrations above 1.0. The spectral changes associated with Hg(II) were identical to Au(III) (results not shown).

TABLE 1

Molar absorption coefficients (ε) of mb and metal-mb.

| Proteins | $\epsilon_{340}$ (mM$^{-1}$cm$^{-1}$) | $\Delta\epsilon_{340}$ (mM$^{-1}$cm$^{-1}$) | $\epsilon_{394}$ (mM$^{-1}$cm$^{-1}$) | $\Delta\epsilon_{394}$ (mM$^{-1}$ cm$^{-1}$) |
|---|---|---|---|---|
| mb | 18.24 | — | 16.07 | — |
| Group A | | | | |
| Cu-mb | 13.55 | 4.69 | 9.75 | 6.31 |
| Au-mb | 9.01 | 9.23 | 7.07 | 9.00 |
| Hg-mb | 11.57 | 6.67 | 12.92 | 3.14 |
| U-mb | 16.24 | 2.00 | 13.98 | 2.09 |
| Group B | | | | |
| Cd-mb | 18.73 | −0.49* | 11.33 | 4.74 |
| Co-mb | 18.60 | −0.36* | 12.78 | 3.29 |
| Fe-mb | 18.17 | 0.07 | 10.19 | 5.88 |
| Mn-mb | 20.54 | −2.30* | 11.28 | 4.79 |
| Ni-mb | 17.88 | 0.36 | 12.21 | 3.86 |
| Zn-mb | 19.69 | −1.45* | 11.13 | 4.94 |

*An increase in absorbance was observed

The spectral changes at 302 nm following the addition of Ag(I) were identical to Au(II) with an initial increase a Ag(I) to mb ratios ≤0.3 Ag(I) per mb, followed by a decrease at higher Ag(I) to mb ratios. The spectral shifts at 340 nm following the addition of Ag(I) were also similar to Au(II) and Hg(II) with a red shift to 367 nm, however, the changes in absorption were opposite to that observed with Au(III), with an initial decrease in absorption from HTI nm at Ag(I) concentrations ≤0.3 Ag(I) per mb followed by an increased absorption at higher Ag(I) concentration (FIGS. 3A and 3B). The spectral changes associated with HTI following the addition of Pb(II) resulted in a decrease in absorption along with a spectral shift to 350 nm (results not shown). The results suggest coordination to HTI for all group A metals, but the coordination may differ between members of the group A metals and that the interactions between metal and HTI may change at different metal to mb ratios.

Group B Metals.

Figure 4:
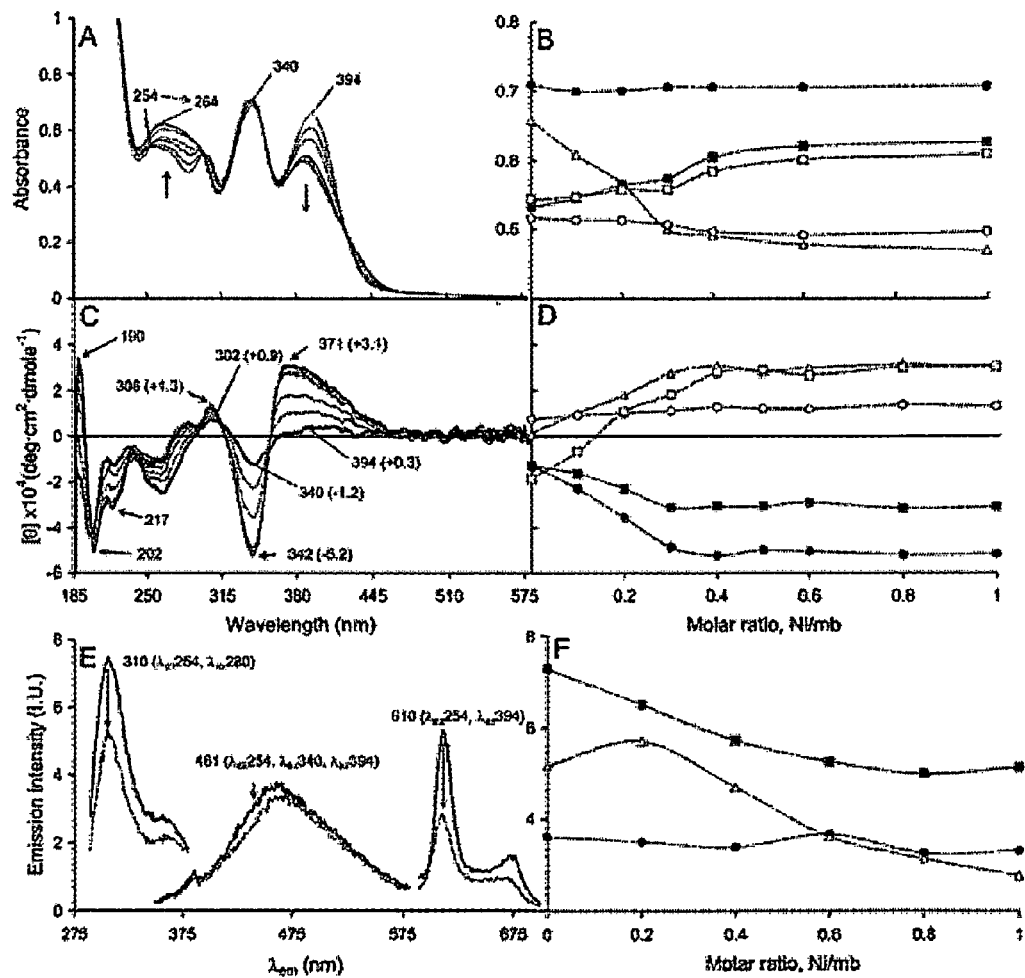
FIG. 4. (A) UV-visible absorption spectra of mb following addition of 0.1, 0.2, 0.3, 0.4, 0.6, 0.8 and 1.0 Ni(II) per mb. Arrows indicate the direction of spectra changes upon Ni(II) additions. (B) Absorption changes at 394 (Δ), 340 (●), 302 (○), 264 (■), and 254 nm (□) following Ni(II) additions. (C) CD spectra of mb as isolated (thick line) and following additions of 0.1 to 1.0 molar equivalents of Ni(II) (thin lines). (D) The effect of Ni(II) addition on the CD spectra at 371 (Δ), 342 (●), 306 (○), 217 (■), and 190 nm (□). (E) Emission spectra of mb in aqueous solution with different excitation wavelength (nm). $\lambda_{ex}$=280, 340, and 394 nm at ambient temperature (thick lines). Arrows indicate the direction of spectrum changes upon Ni(II) additions and thin lines show the spectra upon completion of changes. (F) Emission intensity changes at 610 ($\lambda_{ex}$=394 nm, Δ), 461 ($\lambda_{ex}$=340 nm, ●), and 310 nm ($\lambda_{ex}$=280 nm, ■).

The binding of group B metals by mb resulted in a decreased absorption at 394 nm, with either no change (Ni and Fe), or an increased absorption at 340 nm (Cd, Co, and Zn) (FIG. 4; Table 1). In the case of Mn(II), a blue shift in the maxima of 394 nm to 377 nm following metal addition was also observed (results not shown). In addition, with the exception of Ni(II) and Mn(II), little to no changes in absorbance were observed in the 250-310 nm range for this metal group. Mn(II) addition resulted in an decrease in absorption at 302 nm without an associated increase in absorption at 282 nm. The absence of an absorbance change at 282 nm with decreased absorption at 302 nm suggests the absorption maxima at 282 and 302 nm do not represent the phenolic and phenoxide ion forms of Tyr and may represent a charge transfer band (Choi et al., 2006; Greenstein et al., 1961).

The final spectral changes associated with the binding of group B metals were similar to those observed in the initial coordination to Cu(II) suggesting these metals were bound as a dimer via the THI moieties (FIG. 1) (Choi et al., 2006). To determine if the final coordination of group B metals was a dimer, the concentration of metal associated with mb were determined following exposure to excess metal concentrations. Consistent with the UV-visible absorption titrations, the concentration of Cd(II), Co(II), Mn(II), Ni(II), or Zn(II) bound to mb was approximately half of that observed with Cu(II) demonstrating mb binds these metals as a dimer even in the presses of saturating metal concentrations (Table 2).

TABLE 2

Molar ratios of Cu(II) and group B metals per mb. Mb was treated with saturating concentrations of (50 fold molar excess) of Cu(II) (Cu-mb), Cd(II) (Cd-mb), Zn(II) (Zn-mb), Ni(II) (Ni-mb), Mn(II) (Mn-mb), or Co(II) (Co-mb), collected on a Dianion HP-20 column, washed with 5 column volumes of $H_2O$, then eluted and freeze dried. Standard variance was equal to or less than 20%.

| Metal | mb | Cu-mb | Cd-mb | Zn-mb | Ni-mb | Mn-mb | Co-mb |
|---|---|---|---|---|---|---|---|
| Cu(II) | 0.0376 | 1.552 | bd | 0.0014 | 0.0010 | 0.0002 | bd |
| Cd(II) | 0.003 | 0.0006 | 0.6079 | bd | bd | bd | 0.0008 |
| Zn(II) | 0.001 | bd* | bd | 0.6575 | 0.0017 | 0.0040 | bd |
| Ni(II) | 0.0001 | 0.0029 | 0.0005 | 0.0002 | 0.7603 | 0.0004 | 0.0107 |
| Mn(II) | 0.0004 | bd | bd | 0.0028 | 0.0014 | 0.6778 | 0.0003 |
| Co(II) | 0.0003 | 0.0016 | 0.0017 | 0.0004 | 0.0002 | 0.0001 | 0.8068 |

*below detection

Fluorescence Spectroscopy.

As observed with Cu (Choi et al., 2006), the addition of other group A, and with the exception of Mn(II), group B metals quenched emissions from THI following excitation at 394 nm ($\lambda_{ex394}$) (FIGS. 2E, 2F, 3E, and 3F; Table 3). The addition of Mn(II) had no effect on emission from THI (results not shown). With the exception of Co(II) and Mn(II), the addition of group A and B metals also quenched emission from Tyr suggesting Tyr was either involved in metal coordination or was proximal to the metal coordination site (FIGS. 2E, 2F, 3E, and 3F; Table 3).

TABLE 3

Change in emission intensities from Tyr, following excitation at 280 nm ($\lambda_{ex}$280 nm), THI following excitation at 394 nm ($\lambda_{ex}$394 nm), and HTI following excitation at 340 nm ($\lambda_{ex}$340 nm) following the addition of equimolar concentrations of metals to methanobactin.

| | Change in Emission Intensity | | |
|---|---|---|---|
| Metal | Tyr 310 nm | HTI 461 nm | THI 610 nm |
| Group A | | | |
| Cu(II)[1] | −4.88[2] | −0.03[2,4] | −3.82[2] |
| | −1.00[3] | −0.83[3] | −1.57[3] |

TABLE 3-continued

Change in emission intensities from Tyr, following excitation at 280 nm ($\lambda_{ex}$280 nm), THI following excitation at 394 nm ($\lambda_{ex}$394 nm), and HTI following excitation at 340 nm ($\lambda_{ex}$340 nm) following the addition of equimolar concentrations of metals to methanobactin.

| | Change in Emission Intensity | | |
|---|---|---|---|
| Metal | Tyr 310 nm | HTI 461 nm | THI 610 nm |
| Group B | | | |
| Cd(II) | −0.43 | +1.76 | −1.72 |
| Co(II) | −0.10 | −0.43 | −1.72 |
| Fe(III) | −4.84 | −0.92 | −3.23 |
| Ni(II) | −2.85 | −0.37 | −2.70 |
| Zn(II) | −0.88 | +0.52 | −4.0 |
| Group C | | | |
| Hg(II) | −4.26 | +1.11 | −3.82 |
| Au(III) | −6.36 | +2.01 | −3.80 |
| Group X | | | |
| Mn(II) | +0.17 | −0.44 | +0.37 |

[1] from Choi et al. (2006)
[2] as isolated by Choi et al. (2006)
[3] isolated following Cu(II) saturation and Na$_2$EDTA treatment (Choi et al., 2006; Kim et al., 2005)
[4] Note:
Absence of quenching resulted from the reduction of Cu(II) to Cu(I) before coordination to HTI (Choi et al., 2006).

Figure 5:
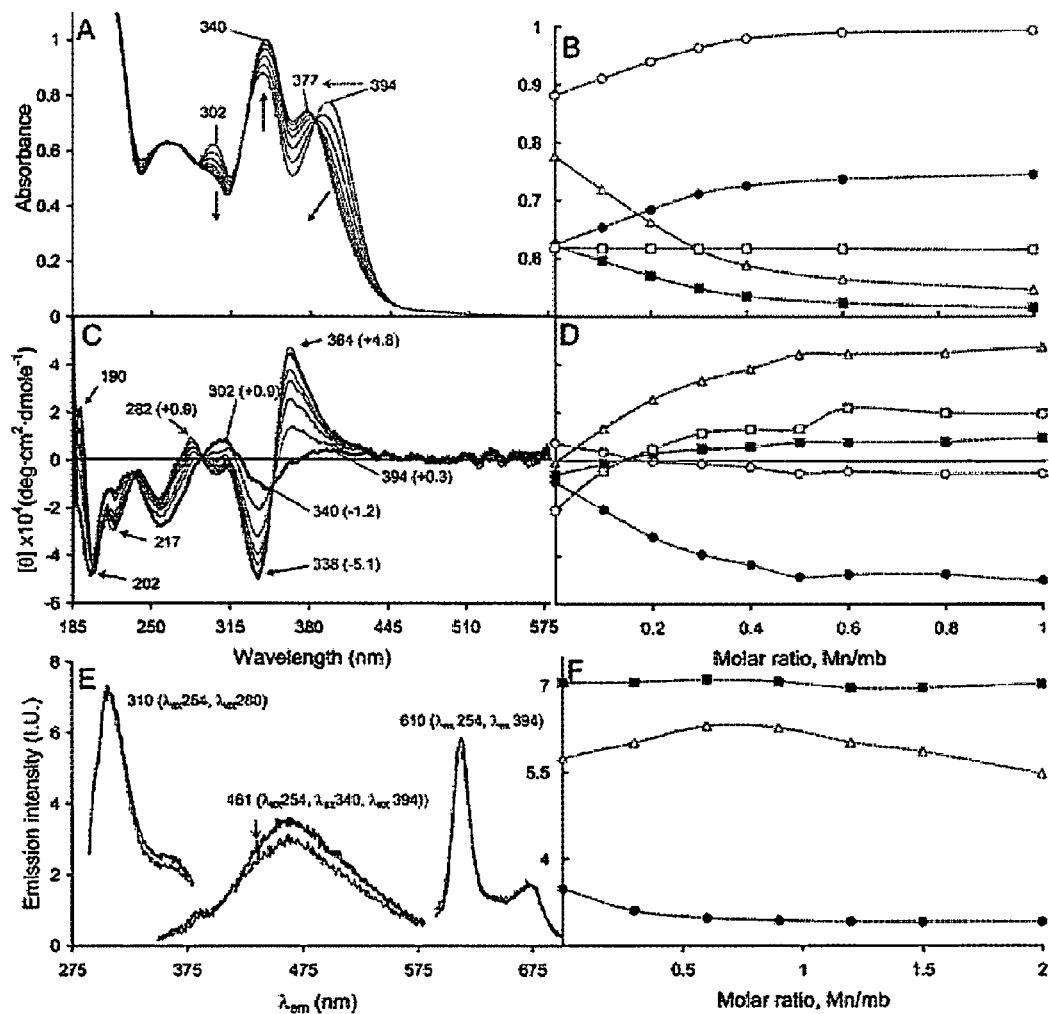
FIG. 5. (A) UV-visible absorption spectra of mb following addition of 0.1, 0.2, 0.3, 0.4, 0.6, 0.8, 1.0, 1.2, 1.4, 1.6. 1.8 and 2.0 Mn(II) per mb. Arrows indicate the direction of spectra changes upon Mn(II) additions. (B) Absorption changes at 394 (Δ), 377 (●), 340 (○), 302 (■), and 254 nm (□) following Mn(II) additions. (C) CD spectra of mb as isolated (thick line) and following additions of 0.1 to 2.0 molar equivalents of Mn(II) (thin lines). (D) The effect of Mn(II) addition on the CD spectra at 364 (Δ), 338 (●), 302 (○), 282 (■), and 190 nm (□). (E) Emission spectra of mb in aqueous solution with different excitation wavelength (nm). $\lambda_{ex}$=280, 340, and 394 nm at ambient temperature (thick lines). Arrows indicate the direction of spectrum changes upon Mn(II) additions and thin lines show the spectra upon completion of changes. (F) Emission intensity changes at 610 ($\lambda_{ex}$=394 nm, Δ), 461 ($\lambda_{ex}$=340 nm, ●), and 310 nm ($\lambda_{ex}$=280 nm, ■).

The addition of groups A and B metals had mixed effects on emission from HTI following excitation at 340 nm (FIGS. 3E and 3F). The addition of Cd(II), Zn(II), Hg(II) and Au(III) to mb resulted in an increase in emission from HTI (FIGS. 4E and 4F) following excitation at 254, 340, or 394 nm. In the case of Au, the emissions observed at 461 nm decreased at Au(III) to mb ratios ≥0.8 following excitation at 254 and 340 nm with new emission maxima at 421, 441, and 524 nm following excitation at 394 nm (FIGS. 5A and 5B). These new emission maxima were not observed with excitation at 254 or 340 nm nor were they observed with Hg(III). Cation induced fluorescence has been shown to occur with removal or separation of an internal quencher following cation binding, or via cation binding to the internal quencher (Chae et al., 1992; Czarnik 1992). Cation induced increased fluorescence has also been observed in chlorophyll a in the presence of negatively charged gold nanoparticles (Bazzouk et al., 2005). In this analogy, gold nanoparticles functioned as an electron shuttle from an electron source such as THI to HTI. XPS spectroscopy demonstrated the reduction of Au(III) to Au(0) and examination of Au-mb complexes by transmission electron microscopy (TEM) and UV-visible absorption spectroscopy showed the formation of nanoparticles at Au to mb ratios above 1.2 Au per mb (see below).

Circular Dichroism Spectroscopy

Figure 2:
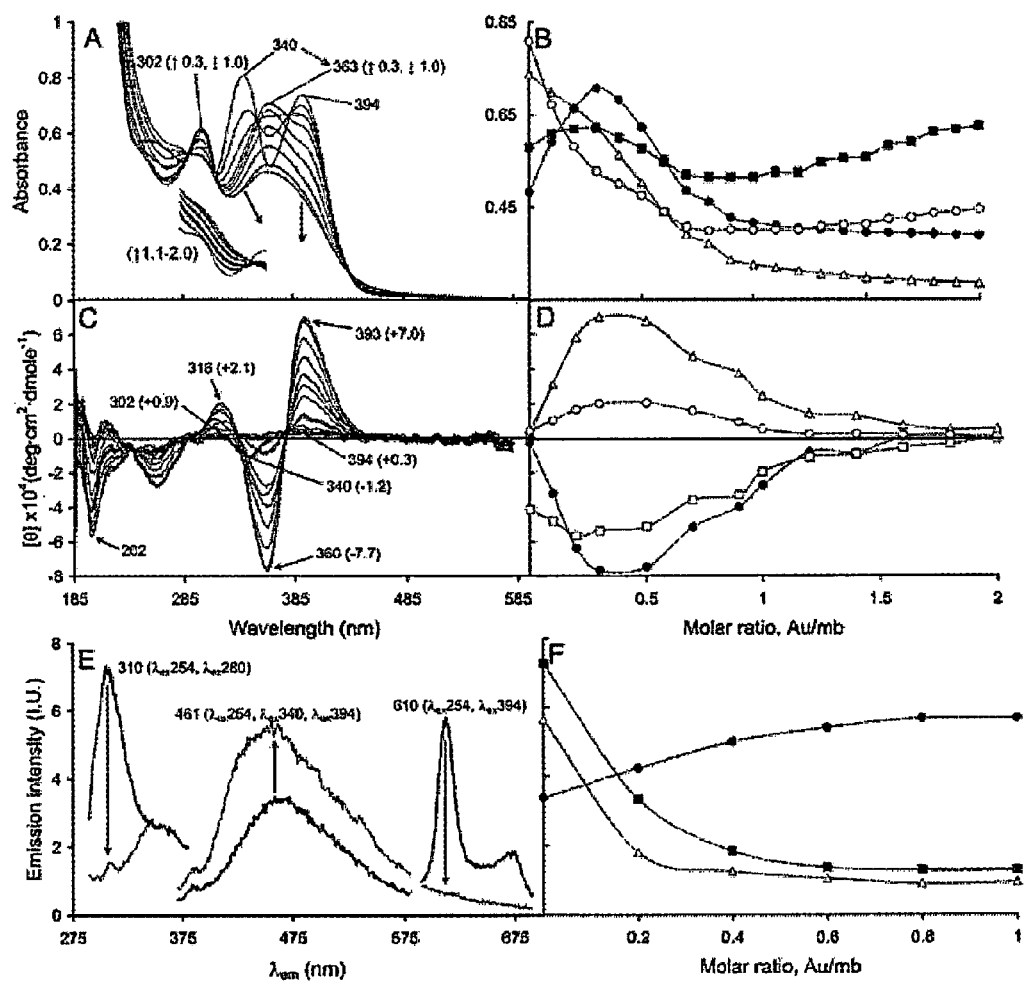
FIG. 2. (A) UV-visible absorption spectra of mb following addition of 0.1, 0.2, 0.3, 0.4, 0.6, 0.8, 1.0, 1.2, 1.4, 1.6. 1.8 and 2.0 Au(III) per mb. Arrows indicate the direction of spectra changes upon Au(III) additions. (B) Absorption changes at 394 (Δ), 363 (●), 340 (○), and 302 (■) following 0.1 to 2.0 Au(III) additions. Due to the development of strong absorption/light scattering below 300 nm with 1.1 to 2.0 Au(III) additions, absorption changes in this region could not be monitored (shown in insertion in panel A). (C) CD spectra of mb as isolated (thick line) and following additions of 0.1 to 2.0 molar equivalents of Au(III) (thin lines). (D) The effect of Au(III) addition on the CD spectra at 393 (Δ), 360 (●), 316 (○), and 202 nm (□). (E) Emission spectra of mb in aqueous solution with different excitation wavelength (nm). $\lambda_{ex}$=280, 340, and 394 nm at ambient temperature (thick lines). Arrows indicate the direction of spectrum changes upon Au(III) additions and thin lines show the spectra upon completion of changes. (F) Emission intensity changes at 610 ($\lambda_{ex}$=394 nm, Δ), 461 ($\lambda_{ex}$=340 nm, ●), and 310 nm ($\lambda_{ex}$=280 nm, ■).

The UV-CD spectrum of mb showed a strong negative band below 200 nm with negative shoulders at 202 (FIGS. 3C and 5C) and 217 nm (FIGS. 2C and 4C), characteristic of an unordered polypeptide (Fasman, 1996). Like the UV absorption spectra, the CD spectra of the group A metals were complex and depended on the metal to mb ratio (FIG. 2). At Au(III) (FIGS. 2C and 2D) or Hg(II) to mb concentrations ≤0.4 metal to mb, the UV-CD spectra was similar to that of Cu (Choi et al., 2006). However, at concentrations of metal to mb >0.5, the trend reversed. The UV-CD spectra of Ag(I) was also complex with the development of an absorption maxima at 288 nm at Ag(I) to mb ratios ≤0.7 Ag(I) per mb followed by a red shift to 298 nm at Ag(I) to mb ratios between 0.7 and 0.9 Ag(I) per mb. At Ag(I) to mb ratios ≥0.9 nm, the absorption intensity at 298 nm does not change, but a new absorption maxima at 318 nm was observed. The absorption maxima between 286 and 318 nm may represent both changes in both the environment and oxidation state of the Tyr. Addition of group B resulted in positive band enhancements at 190 nm, suggesting the development of α-helical characteristics (FIGS. 4C and 4D).

The visible CD spectra following metal binding showed the development of an exciton coupled spectrum between the two-chromophore system (THI and HTI) with all metals tested (FIGS. 2-5). The CD spectra in the 315 to 415 nm region following metal additions were consistent with a Cotton effect involving the THI and HTI (Fasman, 1996; Berova et al., 2000; Crews et al., 1998). At molar ratios <0.3 Au(III) or Hg(II) per mb, the visible-CD spectra were similar to that observed following copper addition (FIGS. 3C, 3D, 4C & 4D) (Choi et al., 2006). The CD-spectra associated with HTI following the addition of Au(III) or Ag(I) resulted in a red shift from 340 nm to 360 and 354 nm, respectively, which were similar to that observed in the UV-visible absorption spectra, with an associated negative band enhancement. The CD-spectra from THI showed a positive band enhancement with little or no shift in the absorption maxima. The absence of a shift in the absorption maxima of both THI and HTI in the CD-spectra suggest little to no change in the hydrophobicity of the environment of these groups following metal binding. In contrast to Cu (Choi et al., 2006), little change in the visible CD spectra was observed at Au(III) or Hg(II) to mb ratios between 0.3 and 0.5 (FIGS. 2C and 2D) and between 0.3 and 0.6 Ag(I) per mb (FIGS. 3C and 3D) suggesting little to no changes in the orientation between THI and HTI occurred in this concentration range. At Au(III) or Hg(II) concentrations >0.5 per mb, the trends throughout the visible CD-spectra reversed and with the exception of the spectral shift of HTI, the spectra at 2.0 Au(II) or Hg(II) per mb were similar to metal free mb. At Ag(I) to mb ratios >0.6, the spectral changes were essentially opposite to that observed with Au(II) or Hg(II) (FIGS. 3C and 3D).

In group B a negative band enhancement near 340 nm (2nd Cotton effect, HTI) and a positive band enhancement between 360 nm and 370 nm (1st Cotton effect, THI) were observed with metal addition suggesting the two chromophores were brought together with a counter-clockwise twist (positive chirality) (FIGS. 4C and 4D). In contrast to Cu (Choi et al., 2006), the absorbance maxima associated with HTI following the addition of group B metals remained near 340 nm, suggesting the hydrophobicity of the environment around HTI did not change following metal binding. The absorption maxima associated with THI showed a blue shift indicating THI moved to a more hydrophobic environment following the binding of groups B metals. This spectral shift was opposite to the at observed with Cu suggesting the conformation changes associated with the binding of group B metals were in an opposite rotation to the changes associated with the coordination of Cu(II) or Cu(I) (Choi et al., 2006).

Figure 3:
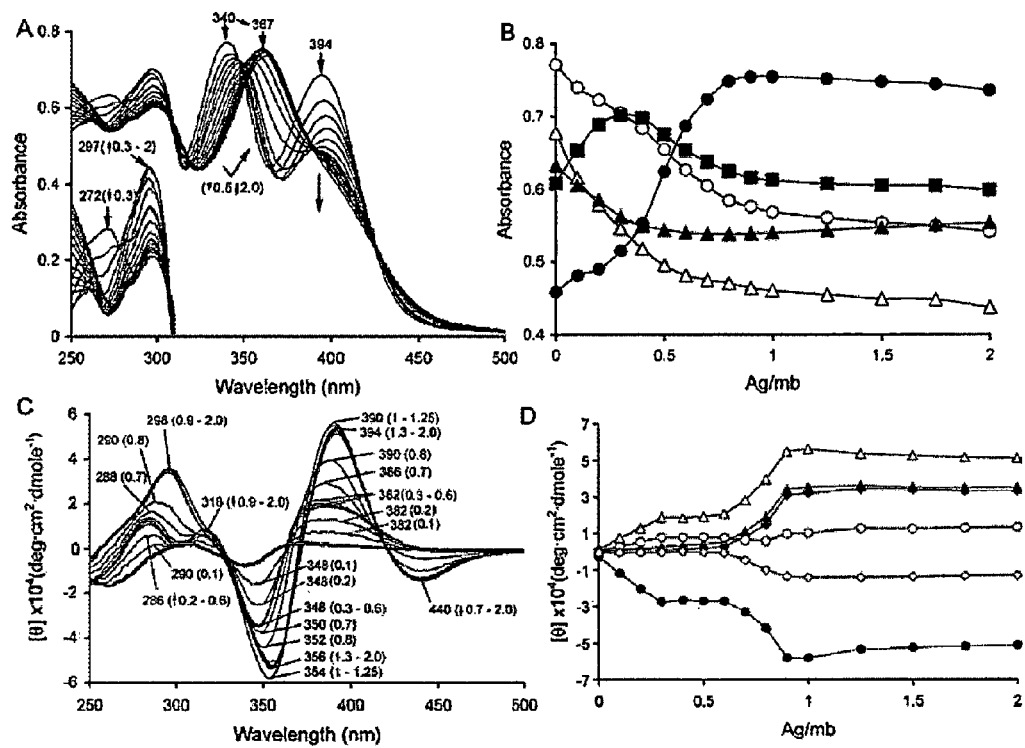
FIG. 3. (A) UV-visible absorption spectra of mb following addition of 0.1, 0.2, 0.3, 0.4, 0.6, 0.8, 1.0, 1.25, 1.4, 1.6. 1.8 and 2.0 Ag(I) per mb. Arrows indicate the direction of spectra changes upon Ag(I) additions. (B) Absorption changes at 394 (Δ), 363 (●), 340 (○), 302 (■), 272 (Δ) nm following 0.1 to 2.0 Ag(I) additions. (C) CD spectra of mb as isolated (thick line) and following additions of 0.1 to 2.0 molar equivalents of Au(I) (thin lines). (D) The effect of Au(I) addition on the CD spectra at 404 (◇), 390 (Δ), 354 (●), 314 (○), and 300 (♦), 283 (■) nm.

In contrast to copper (Choi et al., 2006), no strong relationships between Tyr and HTI were observed in the CD spectra following the addition of other group A and groups B metals (FIGS. 2-4).

Electron Paramagnetic Resonance (EPR) and X-Ray Photoelectron Spectroscopy (XPS): Oxidation State of Metals Bound to Methanobactin (mb).

Figure 6:
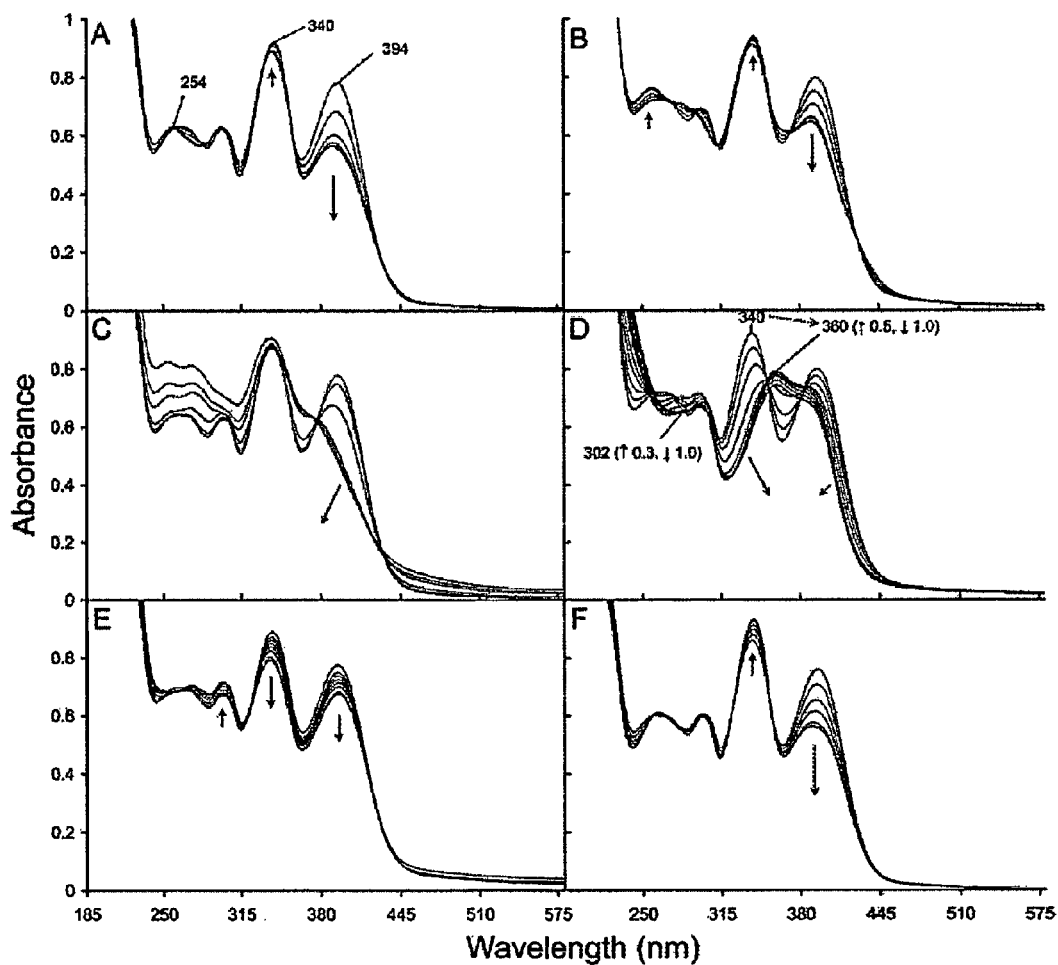
FIG. 6. UV-visible absorption spectra of mb following addition of 0.1 to 1.0 Cd(II) atom (A), Co(II) atom (B), Fe (III) atom (C), Hg(II) atom (D), U(IV) atom (E), or Zn(II) atom (F) per mb. Arrows indicate the direction of spectra changes and dotted arrow indicates the shift of absorption maxima upon metal additions.

X-band EPR spectra of Fe-mb, Co-mb, and Mn-mb samples suggest metal coordination, but not reduction by mb (FIG. 6). Ferric saturated mb samples showed a narrowing of the g=4.3 peak suggesting coordination and possible cluster formation similar to that observed with a variety of siderophores (FIG. 6A). XPS-spectroscopy of Fe-mb complexes confirmed iron associated with mb remained in the ferric state, in contrast to Cu(II) which is reduced to Cu(I). The EPR spectra of Co-mb was narrower than Co(II), again suggesting coordination without reduction (FIG. 6B). Ni-mb showed no Ni EPR signal, which was surprising considering XPS spectra showed the oxidation state Ni(II) did not change following binding to mb.

Figure 7:
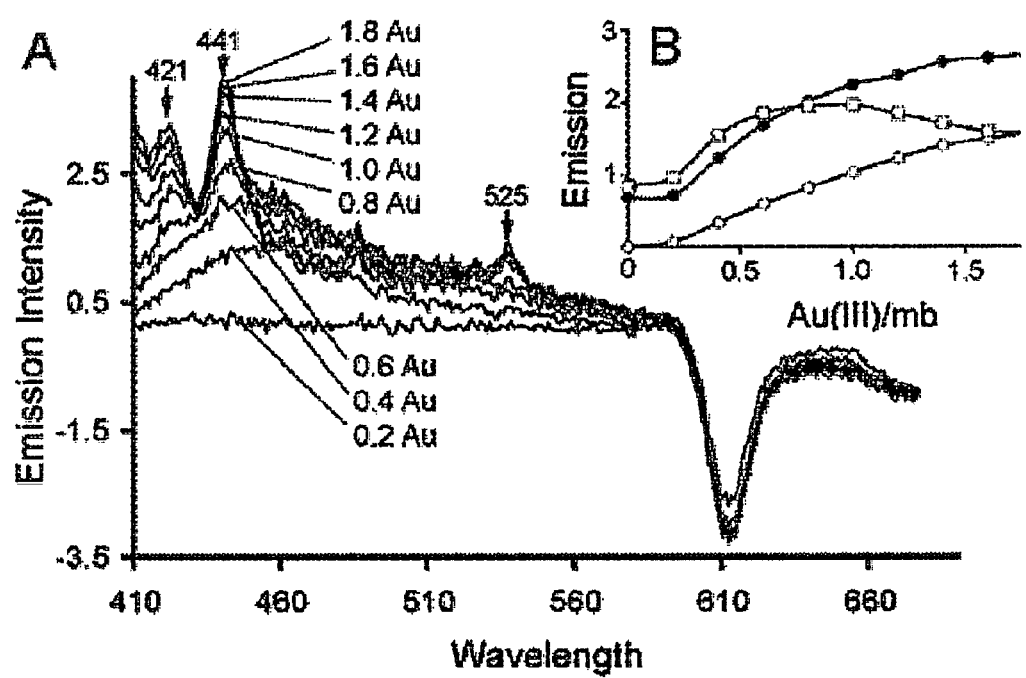
FIG. 7. (A) Difference fluorescence spectra of mb following the addition of 0.2, 0.4, 0.6, 0.8, 1.0, 1.2, 1.4, 1.6, or 1.8 molar equivalences of Au(III) minus mb. (B) Emission intensity changes at 461 nm ($\lambda_{ex}$=394 nm, ○), 421 nm ($\lambda_{ex}$=394 nm, ●), and at 441 nm ($\lambda_{ex}$=394 nm, □).
Figure 8:
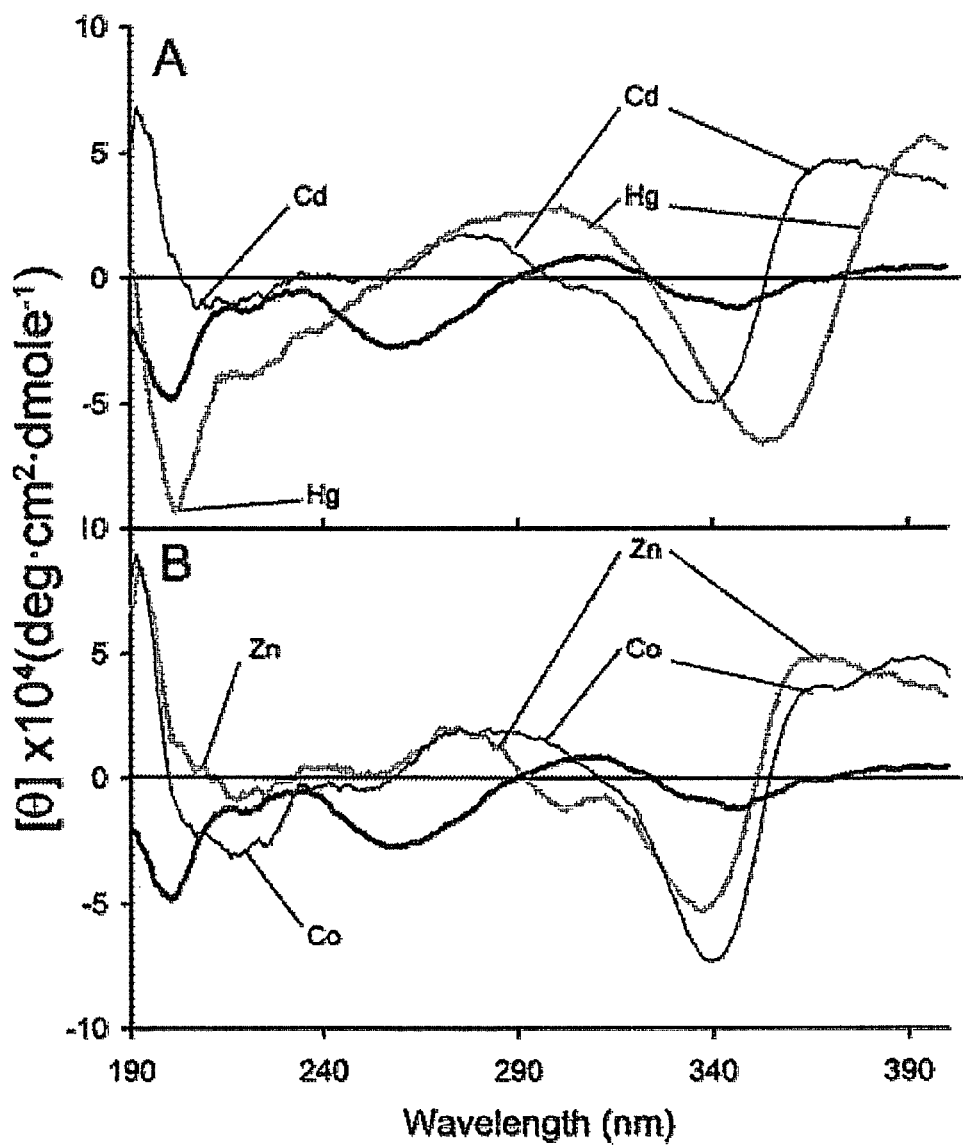
FIG. 8. (A) Circular dichroism (CD) spectra of mb as isolated (thick line) and following addition of 1.0 molar equivalent of Cd(II) (thin line) and Hg(II) (gray line). (B) CD spectra of mb as isolated (thick line) and following addition of 1.0 molar equivalent of Co(II) (thin line) and Zn(II) (gray line).

XPS showed that the group A metal, Au(III), was reduced to Au(0) by mb. Like Cu(II) more than one Au(III) were reduced per mb (Choi et al., 2006) (FIG. 7). In fact, Au(III) was not detected in reaction mixtures until the Au to mb ratio was >2 Au(III) per mb. Examination of Au-mb complexes by transmission electron microscopy (TEM) showed the Au(0) remained associated with mb even at high Au(0) to mb ratios with little to no detection of nanoparticles (FIGS. 8A-8C). However, if samples were centrifuged or subjected to one freeze thaw cycle nanoparticle formation was observed at Au to mb ratios above 1.2 Au per mb (FIG. 9D). Following a freeze-thaw cycle or centrifugation, the nanoparticle size ranged from 2.5 to 30 nm, with the majority (60%) in the 11-20 nm particle range. If Au-mb solutions were examined on formvar coated copper grids nanoparticle formation was also observed (FIGS. 8E and 8F). Nanoparticles formed on copper grids were significantly smaller, average particle size 3.7±1.1 nm, than following centrifugation or a freeze-thaw cycle. The oxidation states of Hg and Ag bound to mb were not determined, but formation of insoluble gray to black precipitates following the addition of Hg(II) or Ag(I) suggested these metals were also reduced by mb.

Figure 9:
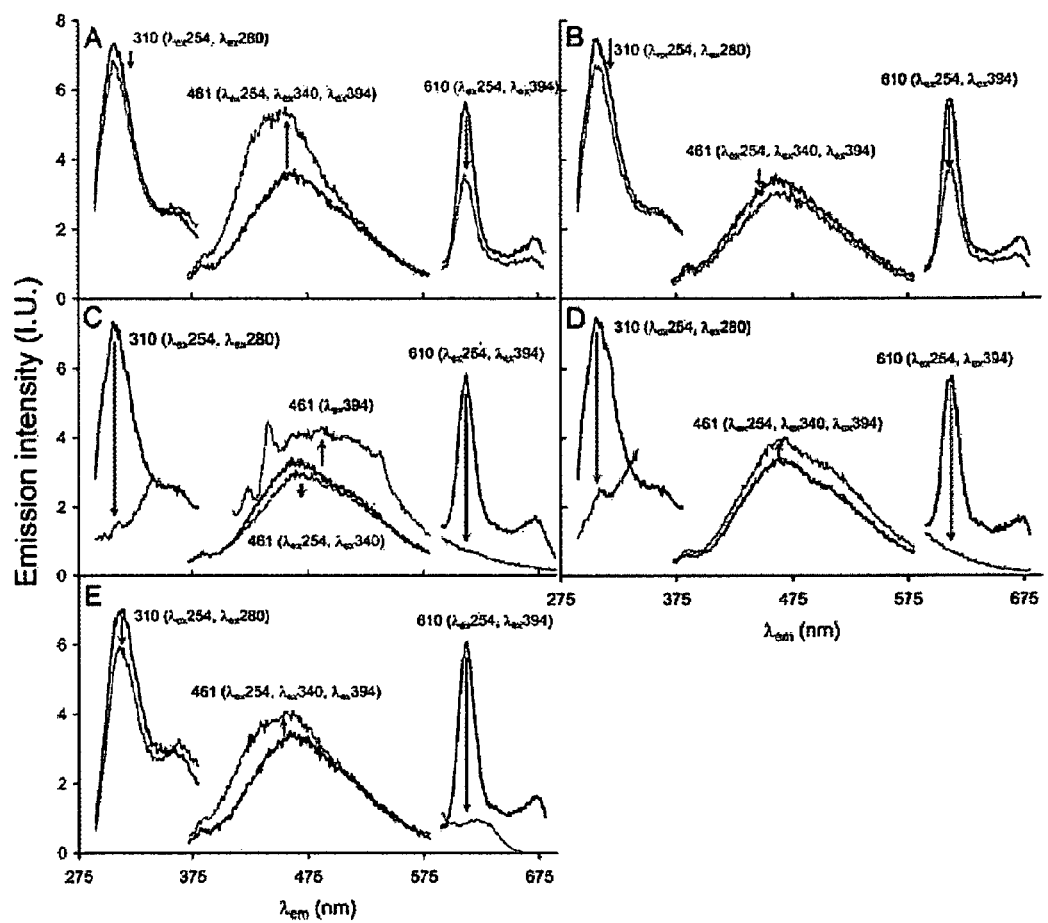
FIG. 9. Emission spectra of mb in aqueous solution with different excitation wavelength (nm). $\lambda_{ex}$=254, 280, 340, and 394 nm at ambient temperature (thick lines). Arrows indicate the direction of spectrum changes upon Cd(II) (A), Co(II) (B), Fe(III) (C), Hg(II) (D), or Zn(II) (E) additions and thin lines show the spectra upon completion of changes.

Metal free mb shows two sulfur signals, one at approximately 163.3 eV which has been assigned to Cys and Met S (Choi et al., 2006; Bain et al., 1989; Riga et al., 1983; Wagner et al., 2005) and one at 161.4 eV (Choi et al., 2006; Bain et al., 1989; Riga et al., 1983; Wagner et al., 2005) which has been attributed to thiocarbonyl S (Choi et al., 2006) (FIG. 9). As with the addition of Cu(II) (Choi et al., 2006), the addition of Au(III) resulted in an increased signal intensity at 163.3 eV and a binding energy shift of the thiocarbonyl S at 161.3 eV. The increased signal intensity at 163.3 eV and the binding energy shift of the thiocarbonyl S were complete at Au:mb ratios ≤0.3 Au per mb suggesting that mb initially binds Au as a tetramer. The similarity in the concentration of Cu(II) (Choi et al., 2006) and Au(III) required to complete the binding energy shift of the thiocarbonyl S was unexpected since Au(III) binding is followed by a three electron reduction and Cu(II) binding results in a one electron reduction suggesting the energy shift in the thiocarbonyl S followed metal binding and not necessary a change in oxidation state. A previous publication (Choi et al., 2006) reported the binding energy shift of the thiocarbonyl S occurred at Cu(II) to mb ratios ≤0.5. However, a more complete titration with Cu(II) has shown the binding energy shift of the thiocarbonyl S was complete at Cu(II) to mb ratios ≤0.3 Cu(II) per mb (results not shown).

Isothermal Titration Calorimetry (ITC).

Figure 10:
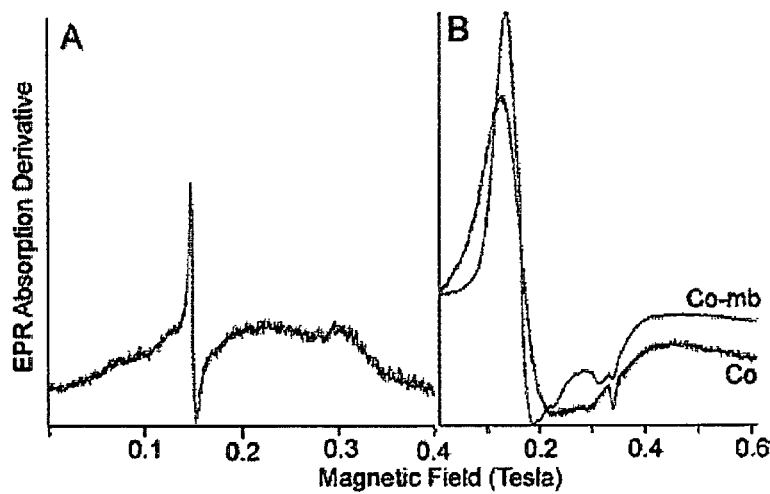
FIG. 10. X-band EPR spectra at 77 K of mb (concentration 4 mM) following the addition of Fe(III) (A), Mn(II) (B) and Co(II) (C) to mb. Experimental conditions: modulation amplitude, 5 G, modulation frequency, 100 KHz, microwave power, 5 mW, temperature 77 K.
Figure 11:
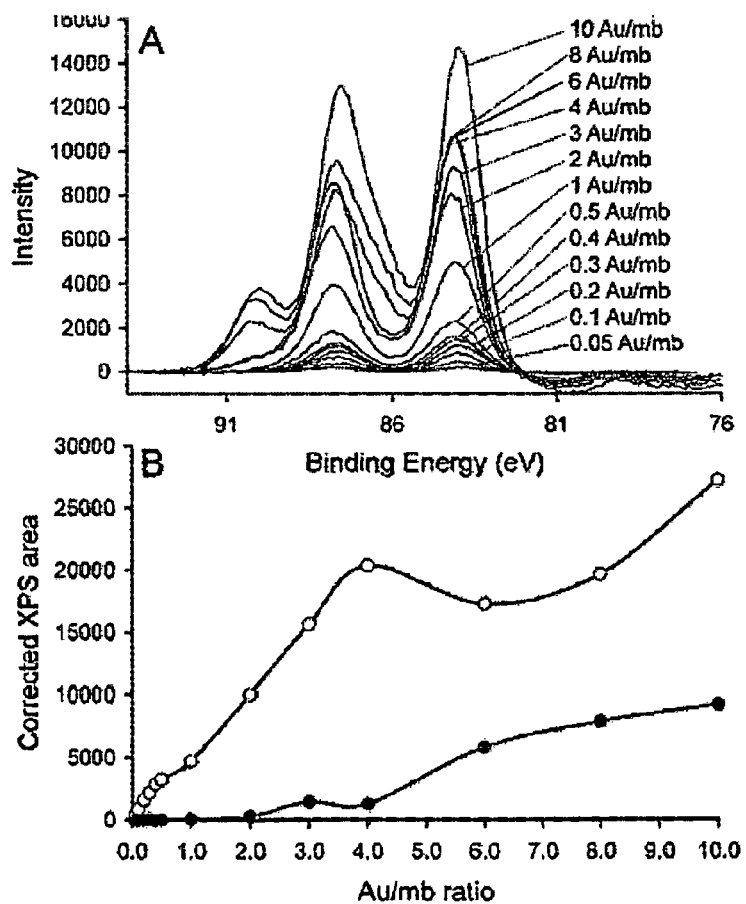
FIG. 11. (A) Gold X-ray photoelectric spectra of mb at gold to mb molar ratios between 0.05 and 10 Au per mb. (B) Corrected signal from Au(0) (○) and Au(III) (●) at different gold:mb molar ratios.
Figure 12:
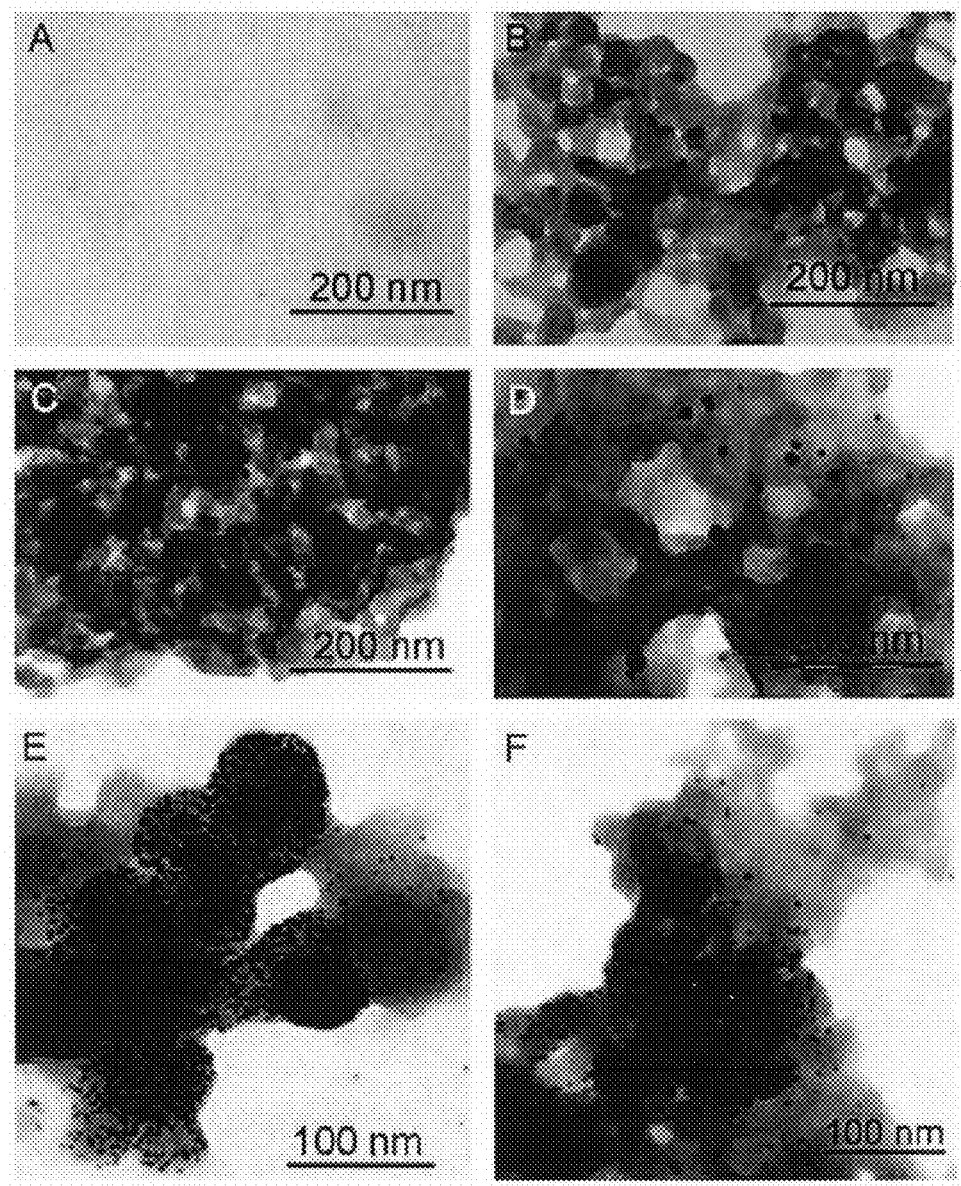
FIG. 12. Transmission electron micrographs of methanobactin solutions following the addition of 1 (A), 1.5 (B), or 2 (C) Au per mb, samples were dried on formvar-coated Ni grids. (D) TEM of 2 Au per mb following one freeze-thaw cycle, samples were dried on formvar-coated Ni grids. TEM of 5(E) and 10(F) Au per mb samples dried on formvar-coated Cu grids. (G) Size range of the mb oligomers as measured by light scattering following the addition of 2 Au per mb.
Figure 12G:
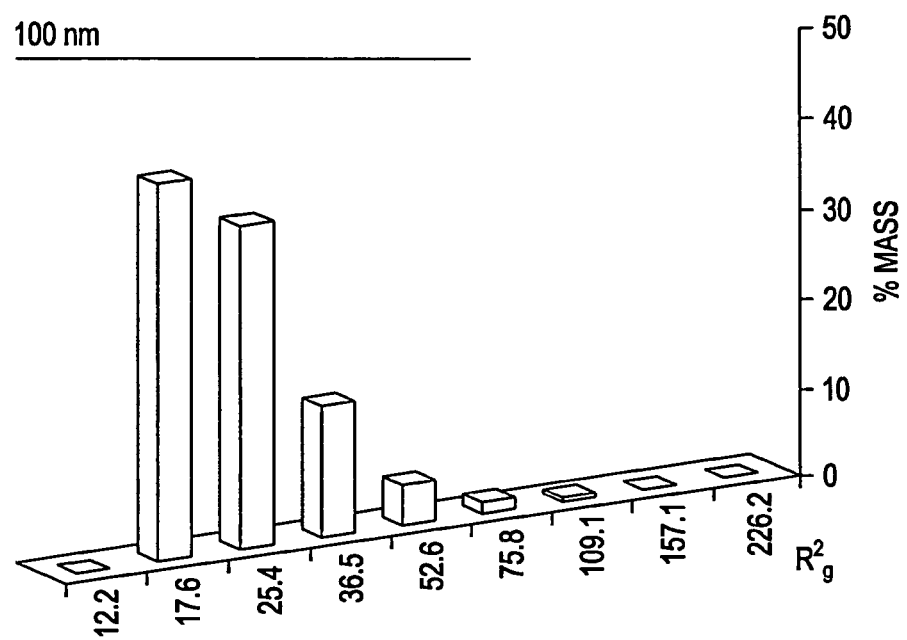
Figure 13:
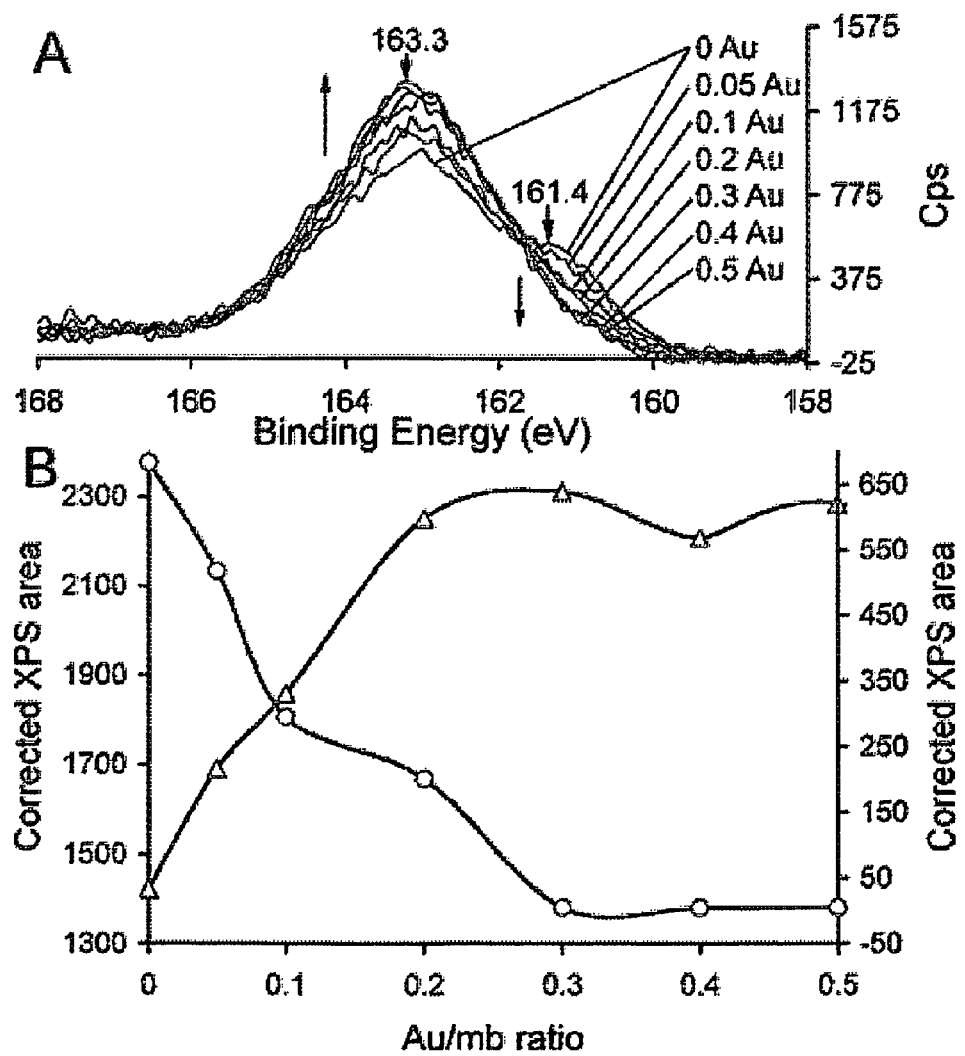
FIG. 13. (A) Sulfur XPS of mb at gold to mb molar ratios between 0.05 and 0.5 Au per mb. (B) Corrected signal from Cys and Met S (Δ) and thiocarbonyl S (○) at different gold: mb molar ratios. Scale on the right is for signal intensity at 163.3 eV and the scale on the left axis is for signal intensity at 161.4 eV. Arrows indicate the direction of spectrum changes upon Au(III) additions.
Figure 14:
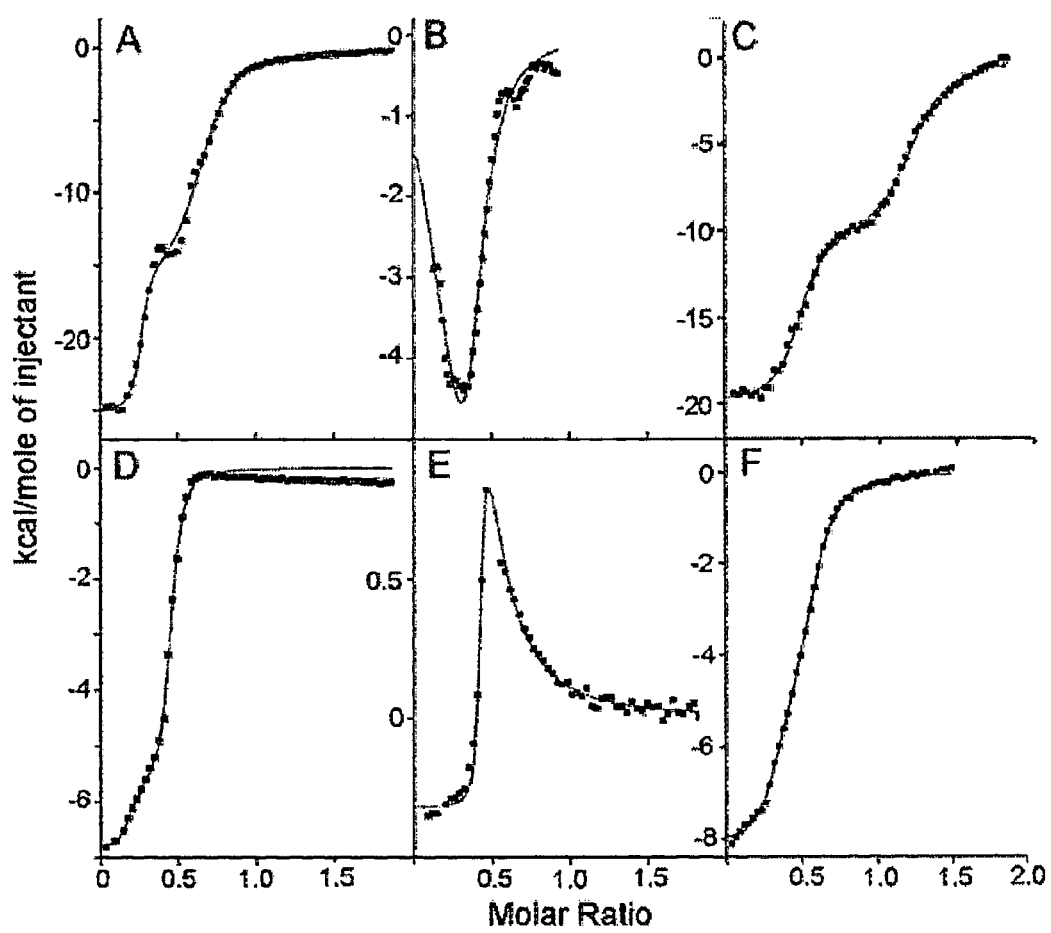
FIG. 14. Binding isotherm of 3.2 mM $HgCl_2$ (A), $HAuCl_4$ (B), $AgNO_3$ (C) $NiCl_2$ (D), $ZnCl_2$ (E) or $FeCl_3$ (F) into 400

With the exception of Co(II), Pb(II) and Mn(II), all of the metals examined fit a two-site binding model better than a one-site binding model (Table 4). Most of the metals followed a titration curves similar to Hg(II) (FIG. 10A), Ni(II) (FIG. 10D) or Ag(I) (FIG. 10C), with extreme transitions observed with Au(III) (FIG. 10B) and Zn(II) (FIG. 10E). The cause for the initial increase in free energy change with increased Au(III) concentration was not determined, but may be associated with the formation of Au(0) nanoparticles (FIG. 9B). The reason for the transition from exothermic to endothermic in Zn(II) titrations was not determined (FIG. 10E). The binding constants observed with non-Cu group A and group B metals were well below the binding constants observed with Cu(II) (Table 4, FIG. 10) and is consistent with its proposed role as a chalkophore (Choi et al., 2006).

TABLE 4

Thermodynamic parameters as measured by ITC for metal binding to mb

| Parameter | Cu(II)[a] | Ag(I) | Au(II) | Hg(II) | Pb(II) |
|---|---|---|---|---|---|
| | | | Group A | | |
| $N_1$(metal mb$^{-1}$) | 0.11 ± 0.003 | 0.47 ± 0.006 | 0.1 ± 0.19 | 0.25 ± 0.005 | 0.61 ± 0.003 |
| $K_1$(M$^{-1}$) | $3.3 \times 10^{34} \pm 3.0 \times 10^{11}$ | $2.6 \pm 0.4 \times 10^7$ | $1.0 \pm 0.5 \times 10^5$ | $9.9 \pm 2.9 \times 10^6$ | $6.84 \pm 0.4 \times 10^5$ |
| $\Delta H_1$(kcal mol$^{-1}$) | −146 | $-2.0 \pm 0.2 \times 10^4$ | $67 \pm 2.6 \times 10^4$ | −25.1 ± 0.02 | $-6.9 \pm 0.04 \times 10^3$ |
| $\Delta S_1$(cal mol$^{-1}$ deg$^{-1}$) | −331 | −32.9 | $2.2 \times 10^5$ | −52.3 | 3.58 |
| $\Delta G_1$(kcal mol$^{-1}$) | −47.2 | −10.1 | $1.44 \times 10^3$ | −9.81 | $-8.0 \times 10^3$ |
| $N_1$(metal mb$^{-1}$) | 0.14 ± 0.01 | 0.75 ± 0.007 | 0.38 ± 0.16 | 0.42 ± 0.01 | — |
| $K_1$(M$^{-1}$) | $2.6 \pm 0.5 \times 10^8$ | $4.7 \pm 0.45 \times 10^4$ | $1.8 \pm 0.2 \times 10^5$ | $89.9 \pm 0.01 \times 10^4$ | — |
| $\Delta H_1$(kcal mol$^{-1}$) | −28.1 ± 0.11 | $-1.1 \pm 0.23 \times 10^4$ | 3.1 ± 0.7 | −16.2 ± 0.05 | — |
| $\Delta S_1$(cal mol$^{-1}$ deg$^{-1}$) | −55.6 | −9.53 | 34.5 | −31.7 | — |
| $\Delta G_1$(kcal mol$^{-1}$) | −11.46 | −7.74 | −7.18 | −6.92 | — |
| $X^2$ | $6.47 \times 10^4$ | $7.14 \times 10^4$ | $3.9 \times 10^5$ | $1.76 \times 10^5$ | $1.27 \times 10^4$ |

| Parameter | Cd(II) | Co(II) | Fe(III) | Mn(II) | Ni(II) | Zn(II) |
|---|---|---|---|---|---|---|
| | | | Group B | | | |
| $N_1$(metal mb$^{-1}$) | 0.2 ± 0.07 | 0.49 ± 0.003 | 0.27 ± 0.007 | 0.54 ± 0.005 | 0.27 ± 0.023 | 0.41 ± 0.004 |
| $K_1$(M$^{-1}$) | $1.3 \pm 0.8 \times 10^6$ | $1.1 \pm 0.2 \times 10^6$ | $9.7 \pm 0.6 \times 10^5$ | $7.7 \pm 1.8 \times 10^5$ | $4.9 \pm 0.9 \times 10^5$ | $4.5 \pm 1.4 \times 10^6$ |
| $\Delta H_1$(kcal mol$^{-1}$) | −3.15 ± 1.7 | −4.08 ± 0.05 | −5.31 ± 0.38 | −0.07 ± 0.001 | −3.15 ± 1.69 | −0.32 ± 0.01 |
| $\Delta S_1$(cal mol$^{-1}$ deg$^{-1}$) | 17.4 | 13.9 | 5.0 | 26.7 | 5.9 | 29.4 |
| $\Delta G_1$(kcal mol$^{-1}$) | −8.34 | −8.22 | -6.80 | −8.02 | −7.75 | −9.08 |
| $N_1$(metal mb$^{-1}$) | 0.22 ± 0.01 | — | 0.3 ± 0.007 | — | 0.18 ± 0.02 | 0.13 ± 0.04 |
| $K_1$(M$^{-1}$) | $1.1 \pm 0.6 \times 10^7$ | — | $1.7 \pm 0.7 \times 10^5$ | — | $1.17 \pm 0.5 \times 10^7$ | $1.8 \pm 0.1 \times 10^4$ |
| $\Delta H_1$(kcal mol$^{-1}$) | −18.96 ± 1.04 | — | −8.15 ± 0.08 | — | −6.89 ± 0.26 | 2.40 ± 0.78 |
| $\Delta S_1$(cal mol$^{-1}$ deg$^{-1}$) | −31.3 | — | 1.14 | — | 9.23 | 27.5 |
| $\Delta G_1$(kcal mol$^{-1}$) | −9.6 | — | −8.49 | — | −9.64 | −5.8 |
| $X^2$ | $1.01 \times 10^5$ | $1.95 \times 10^4$ | $4.70 \times 10^3$ | 9.39 | $2.82 \times 10^4$ | $7.26 \times 10^5$ |

[a]Thermodynamic parameters for Cu(II) were taken from Choi et al. (2006), for comparison purposes the third binding constant for Cu(II) was not included.

Discussion

In contrast to iron siderophores, which are generally specific for Fe(III) (Crosa et al., 2002; Neilands, 1995; Demange et al., 1988; Demange et al., 1990; Neilands; 1983), the results presented here show mb binds a variety of metals. The binding of different metals by mb is intriguing and suggests that although mb preferentially binds copper, mb produced by methanotrophs may play a role in solubilization of many metals in situ. One of the persistent and substantial problems in remediation of hazardous waste sites is the mobilization and transport of radionuclides and heavy metals from these sites to surrounding areas (Anderson et al., 2003; Ehrlich, 1993; Krumholz et al., 2003; Lack et al., 2002; Matsumoto et al., 1999; Parmer et al., 2000; Suzuki et al., 2005). Methanotrophic bacteria are often present at these sites and often used in the remediation of halogenated hydrocarbons (Hanson et al., 1996). The results presented herein indicate they may also be responsible or involved in the mobilization of radionuclides and heavy metals. For example, studies by Jenkins et al. (1994) showed that soluble extracellular extracts produced by methanotrophs increased the transport of Cd(II) in porous soil columns. On the other hand, the reduction of several group A metals can also result in the metal immobilization.

The mechanism of metal binding by non-Cu group A metals showed a number of similarities originally observed with Cu group. First, at low metal concentrations, mb appeared to bind non-Cu Group A metals as a tetramer or oligomer via THI and HTI. Second, all of Group A metals tested were reduced by mb. Third, at metal to mb ratios between 0.25 and 0.5 metal per mb, the metals are coordinated via a mb dimmer followed by a monomer at equimolar metal to mb concentrations. Fourth, at least in the case of Au, more than one metal atom was reduced per mb. Taken together the results suggest non-Cu group A metals followed a metal binding and reduction scheme similar to copper for all group A metals (FIG. 1). However, the CD-spectra suggest the final conformation changes associated with non-Cu group A metals differed from that observed following copper binding.

The results presented here also suggest the mechanism of binding to group B metals differs from that observed with group A metal. Mb appears to bind group B metals as a tetramer dimer depending on the metal concentration via THI (FIG. 1A, reactions 1 and 2*). With respect to the mechanism of binding, group B metals appear to follow the initial binding step observed with group A metal which also initially binds copper via THI (Choi et al., 2006).

REFERENCES

Adelman et al., *DNA*, 2, 183 (1983).
Anderson et al., *Appl. Environ. Microbiol.*, 69:5884 (2003).
Barazzouk et al., *J. Phys. Chem.*, 109:716 (2005).
Bavaay and Merrifield, "The Peptides," eds. E. Gross and F. Meienhofer, Vol. 2 (Academic Press, 1980) pp. 3-285.
Berova et al., Circular Dichroism; Principles and Applications, 2 ed., Wiley-VCH, New York (2000).
Braum et al., *Trends Biochem. Sci.*, 24:104 (1999).
Chae et al., *J. Am. Chem. Soc.*, 114:9704 (1992).
Choi et al., *Biochemistry*, 45:1442 (2006).
Choi et al., *J. Bacteriol.*, 185:5755 (2003).
Choi et al., *Microbiology*, 151:3417 (2005).
Chou and Talalay, *Adv. Enzyme Regul.*, 22:27 (1984).
Clark-Lewis et al., *Meth. Enzymol.*, 287:233 (1997).
Crews et al., Organic structure analysis, Oxford University Press, New York (1998).
Crosa et al., *Microbiol. Mol. Biol. Rev.*, 66:223 (2002).
Czarnik, Fluorescent chemosensors for ion and molecule recognition., Vol. 538, American Chemical Society, Washington, D.C. (1992).
Dayhoff, M. O., in Atlas of Protein Sequence and Structure, 1972, volume 5, National Biomedical Research Foundation, pp. 101-110, and Supplement 2 to this volume, pp. 1-10.
Demange et al., *Biochemistry*, 27 (1988).
Demange et al., *Biochemistry*, 29:11041 (1990).
Di Lorenzo et al., *J. Bacteriol.*, 186:7327 (2004).
DiSpirito et al., Electron flow during methane oxidation in methanotrophs, in Respiration in Archaea and Bacteria (Zannoni, D., Ed.) pp 141-169, Kluwer Scientific, The Netherlands. (2004).
DiSpirito et al., *J. Bacteriol.*, 180:3606 (1998).
Ehrlich, *Appl. Microbiol. Biotechnol.*, 48:687 (1993).
Erlich, ed., *PCR Technology*, (Stockton Press, NY, 1989).
Fasman, Circular Dichroism and the Conformational Analysis of Biomolecules, Plenum Press, New York (1996).
Fitch et al., *Appl. Environ. Microbiol.*, 59:2771 (1993).
Greenstein et al., Chemistry of the Amino Acids, Vol. 2, John Wiley & Sons, Inc., New York (1961).
Hamilton et al., *Ann Rheuma. Dis.*, 60:566 (2001)
Hanson et al., *Microbiol. Rev.*, 60:439 (1996).
Jenkins et al., *Appl. Environ. Microbiol.*, 60:3491 (1994).
Kim et al., *Biochemistry*, 44:5140 (2005).
Kim et al., *Science*, 305:1612 (2004).
Krumholz et al., *Geomicrobiol. J.*, 20:61 (2003).
Lack et al., *Appl. Environ. Microbiol.*, 68:2704 (2002).
Matsumoto et al., *Inorg. Chem.*, 38:1165 (1999).
Matzanke et al., Siderophore-Mediated Iron Transport, in Iron Carriers and Iron Proteins (Loehr, T. M., Ed.), VCH Publishers, Inc., New York (1989).
Meienhofer in "Hormonal Proteins and Peptides," ed.; C. H. Li, Vol. 2 (Academic Press, 1973), pp. 48-267.
Merrifield, *J. Am. Chem. Soc.*, 85:2149 (1963).
Morton et al., *Envon. Sci. Technol.*, 34:4917 (2000).
Mullis et al., *Cold Spring Harbor Symp. Quant. Biol.*, 51, 263 (1987).
Needleman and Wunsch, *J. Mol. Biol.*, 48:443 (1970).
Neilands, *Adv. Morgan. Biochem.*, 5:138 (1983).
Neilands, *J. Biol. Chem.*, 270:6723 (1995).
Nguyen et al., *J. Biol. Chem.*, 273:7957 (1998).
Parmer et al., *Chem. Geol.*, 169:281 (2000).
Pearson and Lipman, *Proc. Natl. Acad. Sci. (U.S.A.)*, 85:2444 (1988).
Phelps et al., *Appl. Environ. Microbiol.*, 58:3701 (1992).
Sambrook et al., *Molecular Cloning: A Laboratory Manual* (Cold Spring Harbor Laboratory Press, N.Y. 1989).
Smith and Waterman, *Adv. Appl. Math.* 2:482 (1981).
Stewart et al., *Solid Phase Peptide Synthesis*, W. H. Freeman Co., San Francisco (1969).
Suzuki et al., *Appl. Environ. Microbiol.*, 71:1790 (2005).
Tellez et al., *Appl. Environ. Microbiol.*, 64:1115 (1998).
Van Roon et al., *J. Rheumatol.*, 32:978 (2005).
Ward et al., *PLoS Biol.*, 2:e303 (2004).
Zahn et al., *J. Bacteriol.*, 178:1018 (1996).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A substantially pure preparation comprising isolated complexes of Au(0) and methanobactin prepared by contacting an amount of Au(III) and an amount of isolated methanobactin in a ratio of Au(III) to methanobactin of >1 and up to 5 in an aqueous composition, effective to yield a mixture in which at least a portion of the Au(III) is reduced to Au(0); and isolating complexes of Au(0) and methanobactin from the mixture.

2. A preparation comprising gold particles having a diameter of greater than about 1.0 nm complexed with methanobactin prepared by contacting an amount of Au(III) and an amount of isolated methanobactin in an aqueous composition, wherein the ratio of Au(III) to methanobactin in the composition is >1 and up to 5, effective to yield a mixture in which at least a portion of the Au(III) is reduced by methanobactin to gold nanoparticles.

3. A method to treat rheumatoid arthritis comprising: administering to a mammal in need thereof an effective amount of the preparation of claim 1.

4. The method of claim 3 wherein the complexes are orally administered.

5. The method of claim 3 wherein the complexes are parenterally administered.

6. The method of claim 3 wherein the complexes are intramuscularly administered.

7. An apparatus having a surface and complexes comprising Au(0) and methanobactin coupled to the surface.

8. The apparatus of claim 7 which comprises a carbon tube or sheet.

9. The apparatus of claim 7 which comprises a circuit board.

10. The apparatus of claim 7 which comprises a wire.

11. The preparation of claim 1 wherein the gold particles are from about 0.5 to about 200 nm in diameter.

12. The preparation of claim 1 wherein the gold particles are from about 10 nm to about 50 nm in diameter.

13. A composition comprising complexes of isolated methanobactin and Au(0).

14. A preparation comprising gold particles having an average diameter of 11 nm complexed with methanobactin, prepared by combining in an aqueous mixture Au(III) and isolated methanobactin, wherein the ratio of Au(III) to methanobactin is >1 up to 5.

15. The method of claim 3 wherein the complexes are intravenously administered.

16. The preparation of claim 2 wherein the gold particles are from about 2.5 to about 30 nm in diameter.

17. The preparation of claim 2 wherein the gold particles are from about 11 nm to about 20 nm in diameter.

\* \* \* \* \*

SEQUENCE LISTING

<160> NUMBER OF SEQ ID NOS: 4

<210> SEQ ID NO 1
<211> LENGTH: 1633
<212> TYPE: DNA
<213> ORGANISM: Ms. trichosporium OB3b
<220> FEATURE:
<221> NAME/KEY: misc_feature
<222> LOCATION: 42
<223> OTHER INFORMATION: n = A,T,C or G

<400> SEQUENCE: 1

```
agcccggctg gttctcgtag gctctcgaaa cggcgcccgg gnacgccggt tctgaccatc      60
gatgtgctga gcgaagcgga gcgccatcgg cttctcgtcg actggaacga cacagccgcc     120
gcctatccgc aggaccgctg cattcatcag ctgttcgagg cgcaggcgag cgagacgccc     180
gacgctgtcg cggtggcgtt cgaggagcaa agcctgacct atgcccaatt gaacgccaga     240
gccaatcggc tggcgcatca tctgcgtcgt ctcggagtag gccccgagac gctggtcggc     300
ctctgcgtcg agcgctcgct cgagatgatc gtcgggctgc tcggcataat gaaggccggc     360
ggcgcctatc tgccgctcga ccccgattat ccggcagatc ggcttgcttt catgctcgcc     420
gacgcgcggc cgctcttgat cctgacgcaa gagcgtctgc gccagcgcct gccgaaggac     480
gccgcgacgc tgagcctgga tgtagaggcc gactggccgt ccatcgccga aagccgcgag     540
gacaatcccg agaatctcgc gcaccccccaa aacctcgcct atgtcatcta cacctccgga     600
tcgacaggca agccaaaagg cgtcggggtc gcgcatgacg gtctcgtcaa tcgcatcgac     660
tggatgcaga agcattatcg cctgaccgat gacgacgtcg tgctacagaa gacgccattc     720
agcttcgacg tatcggtatg ggagttttc tggcctcttc tgaccggcgc ccgtctcgtc     780
ctcgccgcgc cgggcgatca tcgtgagcag ggccgcttgg cgaagctcat cgaaagccgc     840
gcggtcacga ccctgcattt cgtgccgacc atgttgacgg cgttcttgaa cgctgtcgaa     900
gggaagcgga tgcgctcgct tcgccgagtg atctgcagcg gcgaagagct ttccgatagc     960
gccgtctcga agttccatga gatggcgtat cgtgaaaata tggcgtcctg tgagcttcac    1020
aacctctatg gcccaaccga agcctctatc gacgtcacgg cctattgctg cgtcgatgac    1080
ggcggcatcg acagggttcc gatcggccgc ccgatcgcga acacgaaaat ctatcttctc    1140
gacaaggctc tccagccggt tccgataggg gtttcgggcg agctctacat tggcggggtc    1200
ggcctggcgc gaggctatct gaaccgcccc gacctcacgg cggaaagatt tgttccaagc    1260
ccgttcgggg ctcccgggga acgtctctat cggacgggcg atctcgcgcg ctatcgtcgg    1320
gatgggaaca tccaatatct cggccgcgcc gatcatcagg tgaagatccg cgggtttcgc    1380
atcgagctcg gcgagatcga ggcggcgctg gggcgtctgg agacagtgcg cgaagcggca    1440
gcgctggcgc gggaggacga gtcggcgat aagcgcatcg tcgcttatgt cgtctgcgag    1500
gatggggcgg aagcgaatgt cgcgcagctg cgcgcctcgc tggcgaagga tctgcccgac    1560
tatatgatcc cctcggcttt cgttttcctc gacagcttgc cgctgacgca aaatggcaag    1620
atcgaccgca agg                                                         1633
```

<210> SEQ ID NO 2
<211> LENGTH: 2430
<212> TYPE: DNA
<213> ORGANISM: Ms. trichosporium OB3b

<400> SEQUENCE: 2

```
atcgttcgtc aacgcgcatt cgcgcaagct cgacagccat tcgatctcgc gaacggccct    60
gtcattcgcg ttcagctgct gatactcccg tctgtggacg cgaccgcgga tcatgtcctg   120
atcattgttt tccatcatat cgtgaccgac gactggtcgt cggccctatt cttcaacgag   180
ctcgcgacca tttatcctgc gttcgcgagc ggaagaccgt ctcccctgcc agaacccgag   240
ctccaatatg tcgattttgc cgttgctcaa cgcaaatggc tcgacggaga tacgctcgag   300
agacatttag cctattggcg tgaaaagctc gctggcggct ctccctcgat cgatctccca   360
acgcgacgcg atggcgacgc cggattgcag aagaccggtg gcgaggtcca tttcgagatc   420
gctgaaaagg tcaaacgcca attaactcgg ttgagcgagc agagtagtta tacgcgtttt   480
gtcatattca tgtctgcgtt ctacgtattt ctgttccgct acacacacca gaccgacatc   540
tgcgtcgggg cgccgatcgc caaccgcaac ctgcagaag tggaagatat ccagggattc   600
ttcgtcaaca cgctcgtatt gcgcgcaaaa ttgagcggcg atcagcgatt ctccgcattg   660
ctcgagcagg tgcaaaccct tgctctggag gcgcagacac atcaagatct acccttcgag   720
cggctcgtcg aggcgctggg cccacaaatt cgcacattcg ggatcaatcc gcttttccga   780
gtggcgttcg tatttcacaa tatcggtttt gaagacccca aaataccggg attcgatgtt   840
gaaatagtac agggcgtcag acgaaacgcc gtcttcgatc tcgtcttgca cattgccgaa   900
aacgaaaagg ggctgagagg ctggttcgaa tacgatatgg gtttgttcga ggacgcaact   960
gtcgaacgga tggcgcggca cttttcagaat cttctggaga gcgcctcgag caaaagcgac  1020
tcgcggatat cagagctctc tcttttggac gagacggagc gccatcggct tcttgtcgac  1080
tggaacgaca cagccgccgc ctatccgcag gaccgctgca ttcatcagct gttcgaggcg  1140
caggcgagcg agacgcccga cgctgtcgcg gtggcgttcg aggagcaaag cctgaccgat  1200
gcccaattga acgccagagc caatcggctg gcgcatcatc tgcgtcgtct cggagtgggc  1260
cccgagacgc tggtcggcct ctgcgtcgag cgctcgctcg agatgatcgt cgggccgctc  1320
ggcataatga aggccggcgg cgcctatctg ccgctcgatc ccgattatcc gctcgagcgc  1380
ctcgcctata tgctcgccga cgcgcggccg ctggcgatcc tcacgcaaga gcggctgcgc  1440
cagcgtctgc cggacgatgt cgagacgctg agcctcgacg ccgactggcc gtccatcgcc  1500
gaaagccgcg cggacaatcc cgacaatctc gcgcatcccc aaaacctcgc ctatgtcatc  1560
tacacctcgg gaaggacagg caagccgaag ggcgtcgggg tcacgcacca aaatgttcgc  1620
cggctctttg cagccgccga agaggcgttt gattttcct gcgatgatgt ctggacgctg  1680
ttccactcgt ttgcgttcga cttttctgtc tgggagatat ggggcgcgct cctctatggc  1740
ggaaggctga tcatcccgtc ttactgggtg acacgatcgc cggaagcatt ttatgaccta  1800
ttgtgctcac agtccgtcac ggttctgaat cagacgcctt cgagcttcta tcaactatcg  1860
attgtcgatg cggcccgcaa aggaagcgaa ttagagcgct ttccgatcga acggaatcgt  1920
tcgatcgatc agaattcgct caaacgaaag aattctagag gctatccgca tccaatcgga  1980
tcggatagcc ctctatcctc gttgaggctc gttatttcg gtgggaagc tctggaaacc  2040 gggcggctga aggagtggtt cagccgacat ggcgataaac agcctcaact cgtcaacatg  2100
tatggcatca cggaaaccac ggtgcatgtc acattagggc cgctgcagcg cgacagcgca  2160
ggcggagtcg ggcgtcctct cgacgatctc caagcgctca tactcgaccg gagctcgagt  2220
cttctgccca tcggggtttc cggagagctc tacatcggcg gggcggggct cgcgcgaggt  2280
tatctgggcc gagcggatct cacggcgaaa agattcgtcc cccaatccgt tcggagagcc  2340
tggggagcgt ctttaccgc accggcgatc tggcgcgtta tagggcggac ggaaacatcg  2400
```

-continued

| | |
|---|---|
| agtatctcgg ccgcgccgat catcaggtga | 2430 |

<210> SEQ ID NO 3
<211> LENGTH: 2913
<212> TYPE: DNA
<213> ORGANISM: Ms. trichosporium OB3b

<400> SEQUENCE: 3

| | |
|---|---|
| atcgccgtcg tcgccgagga tggatcgctg acctatggcg aattgcgtct gcgcgccaat | 60 |
| caaatcgcgc gcctgctgca acgagcggga atagggccgg agacgcccgt cggcgtgctc | 120 |
| ctcgatcccg gactggatta tgtcgcgtct gtgctcggcg tgctcgtggc gggcggcgcc | 180 |
| ttcgttccgc tggacccggc ctatccgtcg gagcggctgc gttacatgct cgcagattcc | 240 |
| ggcgcgcgcg ccttgatctc cgcgcaaagc ctgccacgcc tcgactgcgt gattcctaag | 300 |
| attctcgtcg acgccgacga gctcgcggat gtttcgaatg acgccgtggt ctccagtgcc | 360 |
| catcccgaca acctcgctta tatcgtctac acctccggct ccacgggagg cgccaaaggc | 420 |
| gtgatggcga cgcatcgcaa tgcggtcgcg tccctcctcg cgcgcttcgc cttctatccg | 480 |
| cagacggtcg acgactttct gcttctctcc tcgctttcct tcgacagctc ctttgcggga | 540 |
| ttattctgga cgctggcgcg cggcggacgg ctccatctcg tcgccgagac gacgcgccgc | 600 |
| gatcccgtcg cgttgaagga gatcatcgcg agccgcgaca tcacccattt cctctgtctc | 660 |
| ccctccttcc accgcgagct gctcggagag ctctcgcgcg gagagcggac gatgctgaaa | 720 |
| tgctgcatcg tcgccggcga ggcctgcggc gccgatgtgg tcgagcgcca ttttcacacg | 780 |
| cttccagaag cagcgctgat caatgaatat ggtccgacgg aatgctcggt ctggtgcgcc | 840 |
| gccgagcagc tgagcacgga agacgatctc tcatcgggcg tcagcatcgg ccgcgcgatt | 900 |
| cccggctctc gcgcttatgt tctcgatgaa aatggcgaac tcgcgccagt cggaatcgcc | 960 |
| ggcgagctct gcgtgggcgg agcaggagtc gcgcgcggct atcgcggcgg cgcggagctg | 1020 |
| accgcgacga aattcacacc cgatccgttc ggcttcggcg agcgtctcta tcgcaccggg | 1080 |
| gatcgcgcga gatatcgcgc ggatggaaag ctcgaattca tgggccgctc cgaccagcag | 1140 |
| gtgaagattc gcggtcatcg catcgaaatc tccgaagtgg aggatgtgct gtcgcgactg | 1200 |
| cccggcgtcc gcgaggcggc ggtcgtggcg cgagccgacg caaccggaga caagcggctc | 1260 |
| gtcgcttatg tcgtcggcga gctcgagccg cgggcggtga agaggcgtt tcgaagcgag | 1320 |
| gccccgcact atatgacgcc gcatttcgtc gtggcgctgc agcgcctgcc gcggctcgac | 1380 |
| aatggcaagg tcgatcgcaa ggcgcttccc gcgccggacg tcgacgcttt gcttagcgaa | 1440 |
| cgctatgtcg cgccgacgac cgagacggaa gcagcgatct gcgccgtgtt cgccgagacg | 1500 |
| ctcggcctcg cgcgcgtcgg cgccgacgac gacttcttcg atctcggcgg cgattcgatc | 1560 |
| cgcgcaattc aggcggcgag cgcgctgaga ctgcgaggat atgaggcggc gccgcgcgat | 1620 |
| ttcttccaat atccgaccgc agcgtctctc gctccgcgcc tgcgcgtcgc gaaagacggg | 1680 |
| acggagccga ctcgcgagcg gcgttcgacg cccttctctc tcgcccagct cggcgcaacc | 1740 |
| gatgtcgagc gattgaaggc tgtgcatggt gacgctcagg atatatatcc gctcacgccc | 1800 |
| atgcaggaag gcatgttgtt ccatgcgctc tcgcagcagg ggaccggcct ctatctgatg | 1860 |
| caggaccgct acgagatcaa aggcgcgctc gatatcgacg ccttcctaga agcgtggcgg | 1920 |
| cgcgttatcg accggcacga cattctacgc acctccttcg actggtcgag cgaaggacgg | 1980 |
| ccgcatcaaa tcgtgcatcg cgccgcgcg cttcccttcg aggtcacgga tctgagcgga | 2040 |
| gccacggaac aggagcagac gaacgcgatc gatcgcgcgc tcgccgccga aagggaagcg | 2100 |

```
ggcttcgacc tcgcgcaggc gccgctcatg cgcatccgca tctttcgcct cgcagatgat    2160
cgtcacatct gcgtgcgcag cttccatcac atcatattgg acgactggtg cacgtctttg    2220
ctcatcctcg acgttcgccg gcactatgcc gctgtgcgaa agggagaggc cacggaattt    2280
gcgccggcgc cgcagttctg gcgctatatc gaatggatcg cggaacagag cgagcggaca    2340
gccgagcagt tctggcgcgc ccatctcgac ggattcgtcg agccgacgcc gctcgtcggg    2400
gcgaaaccgt cgacacgcga cgccgtctcc ttcgtcgagg atatcgtcgt cgacctttcc    2460
aacgagatgt acgagcggct cagagcgctc gttcagcaac gccggctgac gctgaacact    2520
ttcgtgcaag gagcgctcgc gctcactctc ggacgcgccg gcggggtcga cgatgtcgtc    2580
ttcggcgtca ccgcgtccgg ccggccgatc gatctcgacg gcgccgacgc gacgctcggg    2640
ctattcatca acagcctgcc cttgcgcgtc aggatcgacc gacgcaagcc tgtcatcgat    2700
tggctccgcg agattctcgc ggacaatctc gagatgcgcc aatatgagtt cgttccccag    2760
acgaacatcc agcgctggag cgccatctcg cgctccgacg cgccgctctt ccagcatctg    2820
ctgaccttcg agaacgcgcc gctcgaccca tgccgtgcga aggggagaag gaacgtgatc    2880
gacatcgatc tgctgcagaa ccagccgggc tgg                                 2913

<210> SEQ ID NO 4
<211> LENGTH: 773
<212> TYPE: DNA
<213> ORGANISM: Ms. trichosporium OB3b

<400> SEQUENCE: 4
ccgcggattt tgacctgatg atcggcgcgg ccgagatatt ggatgttccc gtcccgatga      60
tagcgcgcca gatcgcccgt ccgatagagg cgctctccgg gagccccgaa cgggcttgga     120
acaaatctct ccgccgtgag gtcggggcgg ttcagatagc cgcgcgcgag gccggccccg     180
ccaatgtaga gctcgcccga catgccaatc ggcaaaagat gtagatttga gccccgaata     240
tagacttgca gatccctgag aggacgcccg acgccctctg tttcatcagg gcgaatcaat     300
tgccgtgtca catgcacagt ggtttcggtg atgccgtaca tgttgcagag tcgaggccgc     360
gtgtggccgt gccgttcgaa ccaccccttc aacctctcga cttcgagggc ttcgccgcca     420
aaaatgacca gcttcagcga cgacaacccg gcgaggtgaa tcgaatcgac agagtcgaga     480
ttgtagaagt tggatggcgt ttgattgaga accgtgacgg attgcgcgcg taaaagctcg     540
tagaacgcct cgggagatcg cgaaacccaa tagggtacga taataagtct tccgccatag     600
aggagcgcgc cccatatctc ccagacagaa aagtcgaacg caaacgagtg gaacagcgtc     660
cagacatcat cgcaggaaaa atcaaacgcc tcttcggcgg ctgcaaagag ccggcgaaca     720
ttttggtgcg tgaccccgac gcccttcggc ttgcctgtac tcccccacgt gta            773
```